US012672482B2

(12) United States Patent
Kim et al.

(10) Patent No.: US 12,672,482 B2
(45) Date of Patent: Jun. 30, 2026

(54) FLUORENE-BASED COMPOUND, ORGANIC LIGHT-EMITTING DEVICE USING SAME, AND MANUFACTURING METHOD THEREFOR

(71) Applicant: LG Chem, Ltd., Seoul (KR)

(72) Inventors: Ji Hoon Kim, Daejeon (KR); Jaesoon Bae, Daejeon (KR); Jaechol Lee, Daejeon (KR); Doowhan Choi, Daejeon (KR); Sungkyoung Kang, Daejeon (KR); Min Suk Jung, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1056 days.

(21) Appl. No.: 17/784,478

(22) PCT Filed: Jan. 6, 2021

(86) PCT No.: PCT/KR2021/000135
§ 371 (c)(1),
(2) Date: Jun. 10, 2022

(87) PCT Pub. No.: WO2021/141382
PCT Pub. Date: Jul. 15, 2021

(65) Prior Publication Data

US 2023/0098935 A1 Mar. 30, 2023

(30) Foreign Application Priority Data

Jan. 8, 2020 (KR) ........................ 10-2020-0002318

(51) Int. Cl.
*H10K 85/60* (2023.01)
*C07C 211/61* (2006.01)
(Continued)

(52) U.S. Cl.
CPC .......... *H10K 85/633* (2023.02); *C07C 211/61* (2013.01); *C09D 7/63* (2018.01);
(Continued)

(58) Field of Classification Search
CPC ... C07C 211/56; C07C 211/60; H10K 85/633; H10K 50/155; H10K 50/17; H10K 71/12; B05D 3/067
See application file for complete search history.

(56) References Cited

U.S. PATENT DOCUMENTS 11,069,859 B2 * 7/2021 Kang ........................ C09D 7/40
2003/0118866 A1 6/2003 Oh et al.
(Continued)

FOREIGN PATENT DOCUMENTS

CN 108752261 A 11/2018
CN 109232492 A 1/2019
(Continued)

OTHER PUBLICATIONS

Gao et al., Chemical Physics Letters 399 (2004) 337-341.*
Search report from International Application No. PCT/KR2021/000135, mailed Apr. 20, 2021.

*Primary Examiner* — Vu A Nguyen
(74) *Attorney, Agent, or Firm* — Lerner David LLP

(57) ABSTRACT

The present specification relates to a fluorene-based compound of Chemical Formula 1, a coating composition including the fluorene-based compound of Chemical Formula 1, an organic light emitting device using the same, and a manufacturing method thereof
(Continued)

[Chemical Formula 1]

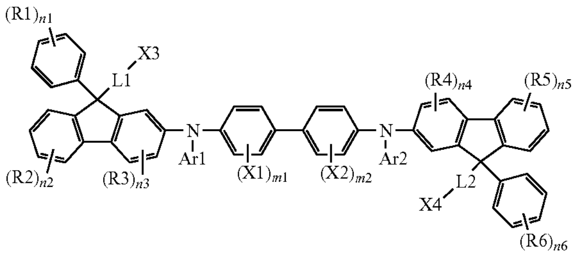

wherein X1 to X4, L1, L2, R1 to R6, Ar1, Ar2, m1, m2, and n1 to n6 are described herein.

15 Claims, 3 Drawing Sheets

(51) Int. Cl.

| | |
|---|---|
| ***C09D 7/63*** | (2018.01) |
| ***H10K 50/15*** | (2023.01) |
| ***H10K 50/17*** | (2023.01) |
| ***H10K 71/00*** | (2023.01) |

(52) U.S. Cl.

CPC ............ *H10K 50/15* (2023.02); *H10K 71/00* (2023.02); *H10K 50/17* (2023.02); *H10K 85/615* (2023.02)

(56) References Cited

U.S. PATENT DOCUMENTS

| | | | |
|---|---|---|---|
| 2004/0067387 A1 | 4/2004 | Kim et al. | |
| 2005/0123796 A1* | 6/2005 | Giesen ................ | H10K 85/631 313/506 |
| 2005/0221124 A1 | 10/2005 | Hwang et al. | |
| 2015/0094437 A1 | 4/2015 | Caille et al. | |
| 2019/0225581 A1 | 7/2019 | Scheible | |
| 2019/0237669 A1 | 8/2019 | Kang et al. | |
| 2020/0028083 A1 | 1/2020 | Kang et al. | |
| 2020/0277502 A1 | 9/2020 | Kang et al. | |
| 2021/0050523 A1 | 2/2021 | Kim et al. | |

FOREIGN PATENT DOCUMENTS

| | | | |
|---|---|---|---|
| CN | 109843850 | A | 6/2019 |
| JP | H11-035532 | A | 2/1999 |
| JP | 2003040844 | A | 2/2003 |
| JP | 2003142269 | A | 5/2003 |
| JP | 2005-290000 | A | 10/2005 |
| JP | 2015511215 | A | 4/2015 |
| JP | 2019532958 | A | 11/2019 |
| JP | 2019537574 | A | 12/2019 |
| KR | 20040028954 | A | 4/2004 |
| KR | 20140107594 | A | 9/2014 |
| KR | 20180099446 | A | 9/2018 |
| KR | 20190056440 | A | 5/2019 |
| KR | 20190136999 | A | 12/2019 |
| WO | 2019/177410 | A1 | 9/2019 |
| WO | 2019/231257 | A1 | 12/2019 |

* cited by examiner

[FIG. 1]
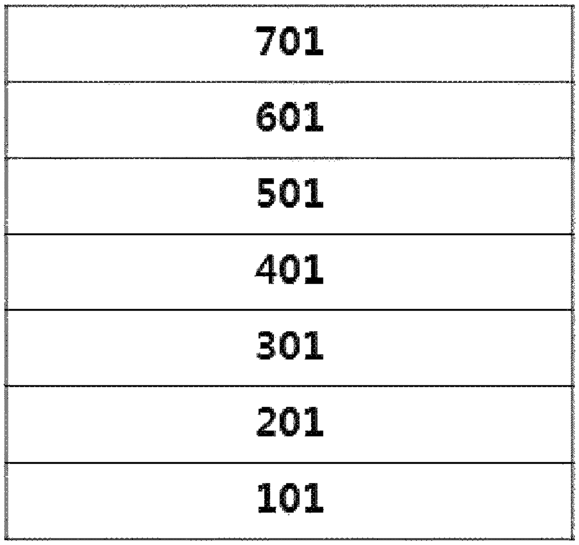
[FIG. 2]
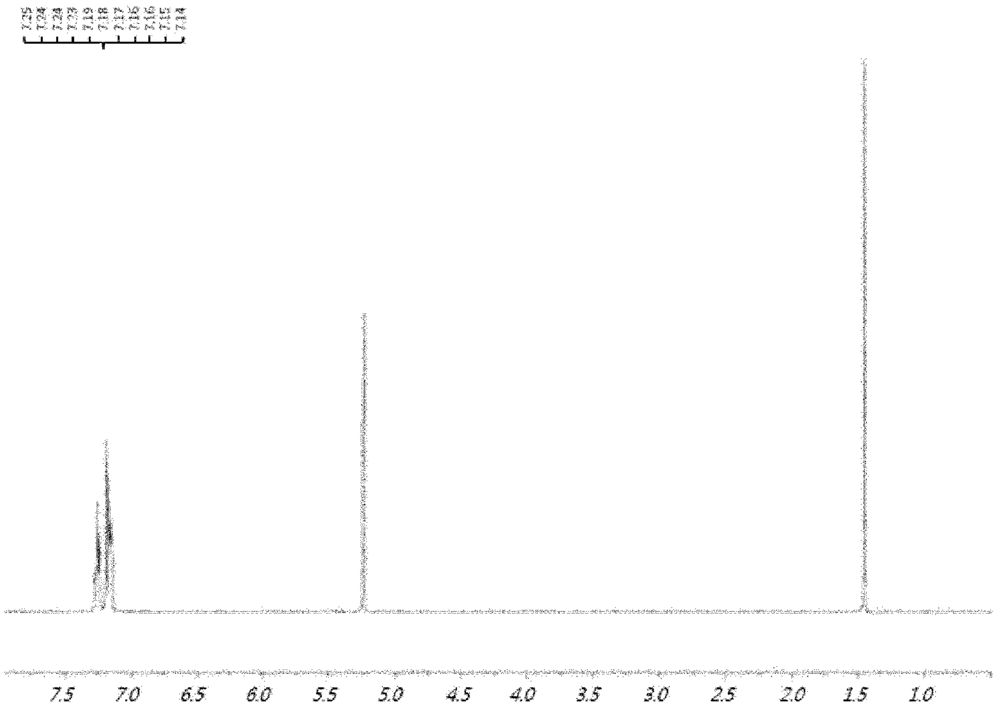

[FIG. 3]
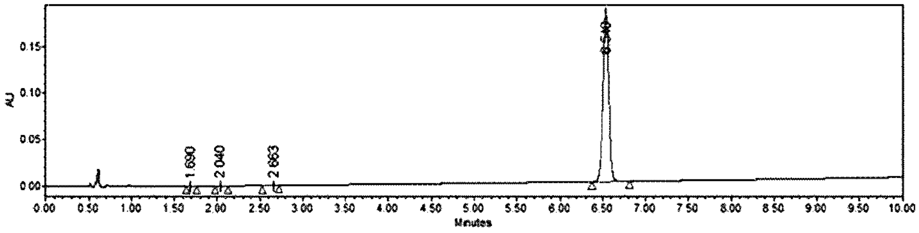
[FIG. 4]
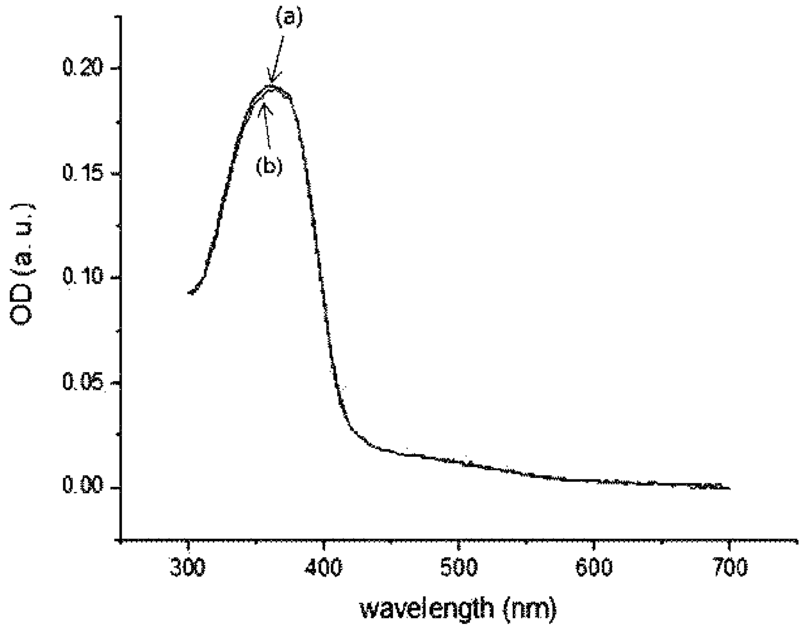

[FIG. 5]
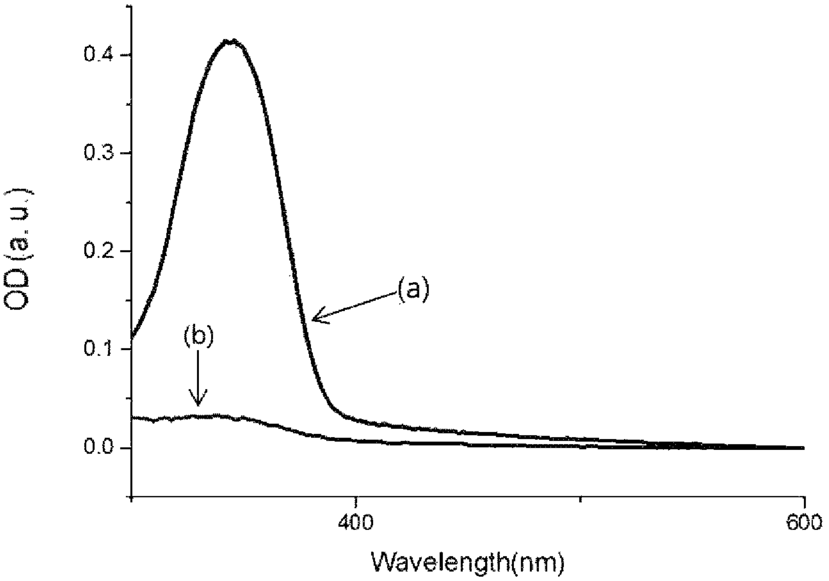

FLUORENE-BASED COMPOUND, ORGANIC LIGHT-EMITTING DEVICE USING SAME, AND MANUFACTURING METHOD THEREFOR

CROSS-REFERENCE TO RELATED APPLICATION(S)

The present application is a national stage entry under 35 U.S.C. § 371 of International Application No. PCT/KR2021/000135 filed on Jan. 6, 2021, which claims priority from Korean Patent Application No. 10-2020-0002318 filed on Jan. 8, 2020, all the disclosures of which are incorporated herein by reference.

TECHNICAL FIELD

The present specification relates to a fluorene-based compound, a coating composition including the fluorene-based compound, an organic light emitting device formed by using the coating composition, and a manufacturing method thereof.

BACKGROUND ART

An organic light emission phenomenon is one of the examples in which an electric current is converted into visible rays through an internal process of a specific organic molecule. The principle of the organic light emission phenomenon is as follows. When an organic material layer is disposed between an anode and a cathode and an electric current is applied between the two electrodes, electrons and holes are injected into the organic material layer from the cathode and the anode, respectively. The electrons and the holes which are injected into the organic material layer are recombined to form an exciton, and the exciton falls down again to the ground state to emit light. An organic light emitting device using this principle may be generally composed of a cathode, an anode, and an organic material layer disposed therebetween, for example, an organic material layer including a hole injection layer, a hole transport layer, a light emitting layer, and an electron transport layer.

The materials used in the organic light emitting device are mostly pure organic materials or complex compounds in which organic materials and metals form a complex, and may be classified into a hole injection material, a hole transport material, a light emitting material, an electron transport material, an electron injection material, and the like according to the use thereof. Here, an organic material having a p-type property, that is, an organic material, which is easily oxidized and electrochemically stable when the material is oxidized, is usually used as the hole injection material or the hole transport material. Meanwhile, an organic material having a n-type property, that is, an organic material, which is easily reduced and electrochemically stable when the material is reduced, is usually used as the electron injection material or the electron transport material. As the light emitting layer material, a material having both p-type and n-type properties, that is, a material, which is stable in both the oxidation and reduction states, is preferred, and when an exciton is formed, a material having high light emitting efficiency for converting the exciton into light is preferred.

In order to obtain a high-efficiency organic light emitting device which is capable of being driven at low voltage, holes or electrons injected into the organic light emitting device need to be smoothly transferred to a light emitting layer, and simultaneously, the injected holes and electrons need to be prevented from being released of the light emitting layer. For this purpose, the materials used in the organic light emitting device need to have an appropriate band gap and HOMO or LUMO energy levels.

In addition, the materials used in the organic light emitting device need to have excellent chemical stability, excellent charge mobility, excellent interface characteristics with electrodes or adjacent layers, and the like. That is, the materials used in the organic light emitting device need to be minimally deformed by moisture or oxygen. Further, the material used in the organic light emitting device needs to have appropriate hole or electron mobility so as to make a balance between densities of holes and electrons in a light emitting layer of the organic light emitting device, thereby maximally forming excitons. Moreover, the material used in the organic light emitting device needs to improve the interface with an electrode including a metal or a metal oxide for the stability of the device.

In addition to those mentioned above, a material used in an organic light emitting device for a solution process needs to additionally have the following properties.

First, the material used in the organic light emitting device needs to form a storable homogenous solution. Since a commercialized material for a deposition process has good crystallinity so that the material is not dissolved well in a solution or easily forms the crystals even though the material forms a solution, it is highly likely that according to the storage period, the concentration gradient of the solution varies or a defective device is formed.

Second, layers in which a solution process is performed need to have resistance to a solvent and a material, which are used during a process of forming other layers, and are required to have excellent current efficiency and an excellent service life characteristic when an organic light emitting device is manufactured.

Therefore, there is a need for developing a new organic material in the art.

DETAILED DESCRIPTION OF THE INVENTION

Technical Problem

The present specification provides a fluorene-based compound, which can be used in an organic light emitting device for a solution process, and an organic light emitting device including the same.

Technical Solution

An exemplary embodiment of the present specification provides a fluorene-based compound represented by the following Chemical Formula 1.

[Chemical Formula 1]

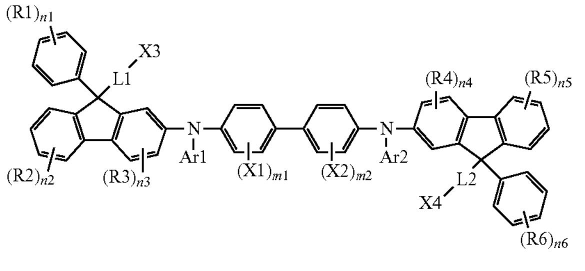

In Chemical Formula 1,

R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, L1 and L2 are the same as or different from each other, and are each independently a direct bond; or a substituted or unsubstituted alkylene group, Ar1 and Ar2 are the same as or different from each other, and are each independently a substituted or unsubstituted aryl group; or a substituted or unsubstituted heteroaryl group, X1 and X2 are the same as or different from each other, and are each independently hydrogen; or a halogen group, and at least one of X1 and X2 is a halogen group, X3 and X4 are the same as or different from each other, and are each independently deuterium; a substituted or unsubstituted alkyl group; a substituted or unsubstituted alkoxy group; a substituted or unsubstituted aryl group; a substituted or unsubstituted heteroaryl group; or a photocurable group or a thermosetting group, m1 and m2 are the same as or different from each other, and are each independently an integer from 1 to 4, n1 and n6 are the same as or different from each other, and are each independently an integer from 0 to 5, n2 and n5 are the same as or different from each other, and are each independently an integer from 0 to 4, n3 and n4 are the same as or different from each other, and are each independently an integer from 0 to 3, and when m1, m2 and n1 to n6 are each 2 or higher, each occurrence of X1, X2, R1 to R6 is the same as or different from each other.

Further, an exemplary embodiment of the present specification provides a coating composition including the fluorene-based compound.

In addition, an exemplary embodiment of the present specification provides an organic light emitting device including: a first electrode;

a second electrode; and an organic material layer having one or more layers provided between the first electrode and the second electrode, in which one or more layers of the organic material layer include the coating composition or a cured product thereof, and the cured product of the coating composition is in a state in which the coating composition is cured by a heat treatment or a light treatment.

Furthermore, an exemplary embodiment of the present specification provides a method for manufacturing an organic light emitting device, the method including: preparing a substrate;

forming a first electrode on the substrate;

forming an organic material layer having one or more layers on the first electrode; and forming a second electrode on the organic material layer, in which the forming of the organic material layer includes forming an organic material layer having one or more layers by using the coating composition.

Advantageous Effects

A core structure of the fluorene-based compound according to an exemplary embodiment of the present specification is substituted with a halogen group. Accordingly, the fluorene-based compound according to an exemplary embodiment of the present specification has a relatively large dipole moment and a relatively low HOMO energy level, compared to a compound having a core structure which is not substituted with a halogen group. Accordingly, the fluorene-based compound according to an exemplary embodiment of the present specification exhibits long service life characteristics when applied to an organic light emitting device.

Further, the fluorene-based compound according to an exemplary embodiment of the present specification forms a stable thin film, which is not damaged in the next solution process, by a heat treatment at 250° C. or less or a UV treatment.

A thin film on which a coating composition including the compound according to an exemplary embodiment of the present specification is applied forms a stable thin film, which is not damaged in the next solution process, by a heat treatment at 250° C. or less or a UV treatment.

The fluorene-based compound according to an exemplary embodiment of the present specification may be used as a material for an organic material layer of an organic light emitting device for a solution process, and may provide low driving voltage, high light emitting efficiency, and high service life characteristics. Further, as the fluorene-based compound is used, the solubility is increased, so that there are advantages in that when an ink of a solution process is prepared, the selection of the solvent is widened, and the melting point and the curing temperature can be lowered.

BRIEF DESCRIPTION OF DRAWINGS

FIG. 1 illustrates an example of an organic light emitting device according to an exemplary embodiment of the present specification.

FIG. 2 is a view illustrating NMR measurement results of Intermediate A-1.

FIG. 3 is a view illustrating HPLC measurement results of Compound 1.

FIG. 4 is a view illustrating the film retention experimental results of a thin film formed by Coating Composition 1 prepared in Experimental Example 1.

FIG. 5 is a view illustrating the film retention experimental results of a thin film formed by Coating Composition 2 prepared in Experimental Example 1.

101: Substrate
201: Anode
301: Hole injection layer
401: Hole transport layer
501: Light emitting layer
601: Electron injection and transport layer
701: Cathode

BEST MODE

In general, since an arylamine-based single molecule used in an organic light emitting device for a solution process does not have resistance to a solvent in the next process, a curing group needs to be introduced into the arylamine-based compound single molecule which can be used in an organic light emitting device for a solution process.

A thin film manufactured by subjecting a coating composition including a fluorene compound, to which an amine group is bonded, according to the present invention to a heat or light treatment provides an organic light emitting device having excellent resistance to a solvent and excellent current efficiency and device characteristics.

Hereinafter, the present specification will be described in detail.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

An exemplary embodiment of the present specification provides a fluorene-based compound represented by the following Chemical Formula 1.

[Chemical Formula 1]

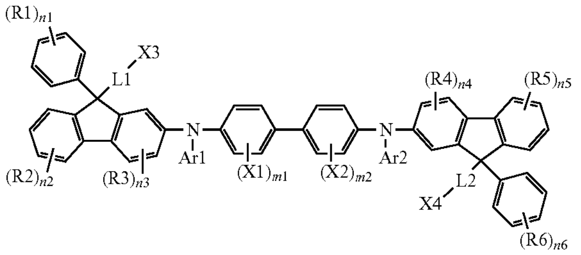

In Chemical Formula 1,

R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, L1 and L2 are the same as or different from each other, and are each independently a direct bond; or a substituted or unsubstituted alkylene group, Ar1 and Ar2 are the same as or different from each other, and are each independently a substituted or unsubstituted aryl group; or a substituted or unsubstituted heteroaryl group, X1 and X2 are the same as or different from each other, and are each independently hydrogen; or a halogen group, and at least one of X1 and X2 is a halogen group, X3 and X4 are the same as or different from each other, and are each independently deuterium; a substituted or unsubstituted alkyl group; a substituted or unsubstituted alkoxy group; a substituted or unsubstituted aryl group; a substituted or unsubstituted heteroaryl group; or a photocurable group or a thermosetting group, m1 and m2 are the same as or different from each other, and are each independently an integer from 1 to 4, n1 and n6 are the same as or different from each other, and are each independently an integer from 0 to 5, n2 and n5 are the same as or different from each other, and are each independently an integer from 0 to 4, n3 and n4 are the same as or different from each other, and are each independently an integer from 0 to 3, and when m1, m2 and n1 to n6 are each 2 or higher, each occurrence of X1, X2, R1 to R6 is the same as or different from each other.

In the present specification, at least one of X1 and X2 is a halogen group. That is, a core structure of the compound represented by Chemical Formula 1 is substituted with one or more halogen groups. Accordingly, the fluorene-based compound according to an exemplary embodiment of the present specification has a relatively large dipole moment and a relatively low HOMO energy level, compared to a compound having a core structure which is not substituted with a halogen group. Accordingly, the fluorene-based compound according to an exemplary embodiment of the present specification exhibits long service life characteristics when applied to an organic light emitting device.

In the present specification, "a thermosetting group or a photocurable group" may mean a reactive substituent which cross-links compounds when being exposed to heat and/or light. The cross-linkage may be produced while radicals produced by decomposing carbon-carbon multiple bonds and cyclic structures by means of a heat treatment or light irradiation are linked to each other.

In an exemplary embodiment of the present specification, the thermosetting group or the photocurable group is any one of the following structures.

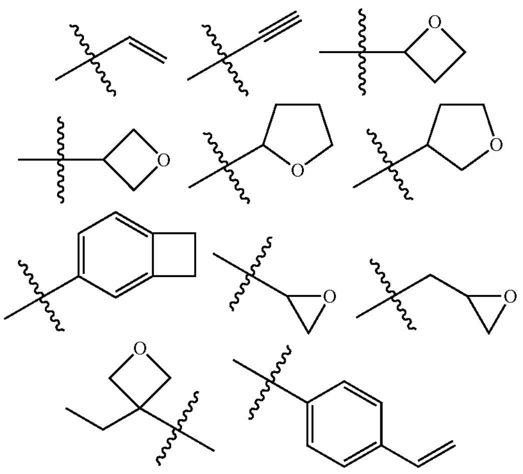

In an exemplary embodiment of the present specification, the fluorene-based compound represented by Chemical Formula 1 can achieve a large area of an organic light emitting device and has an economic effect in terms of time and cost because the device can be manufactured by a solution application method.

Further, when a coating layer is formed by using the fluorene-based compound represented by Chemical Formula 1, the thermosetting group or the photocurable group forms a cross-linkage by heat or light, so that when an additional layer is stacked on an upper portion of the coating layer, it is possible to maintain the coating layer and simultaneously stack the additional layer on the upper portion by preventing the fluorene-based compound included in the coating composition from being washed away by a solvent.

Additionally, in the fluorene-based compound represented by Chemical Formula 1, the thermosetting group or the photocurable group forms a cross-linkage when a coating layer is formed, so that there is an effect in that chemical resistance of the coating layer to the solvent is enhanced and the film retention rate is high.

Furthermore, a fluorene-based compound in which a cross-linkage is formed by a heat treatment or light irradiation according to an exemplary embodiment of the present specification has an effect in that the thermal stability is excellent because a plurality of fluorene-based compounds is cross-linked, and thus the cross-linkage is provided in the form of a thin film in the organic light emitting device.

Hydrogen or deuterium may be bonded to a position where a substituent is not bonded to the compound described in the present specification.

In the present specification,

and - - - - - - mean a moiety bonded to another substituent or a bonding portion.

In the present specification, the term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or more substituents selected from the group consisting of deuterium; a halogen group; a nitrile group; a nitro group; an alkyl group; an alkoxy group; an aryl group; and a heteroaryl group, or being substituted with a substituent to which two or more substituents among the substituents exemplified above are linked, or being unsubstituted. For example, "the substituent to which two or more substituents are linked" may be a biphenyl group. That is, the biphenyl group may also be an aryl group, and may be interpreted as a substituent to which two phenyl groups are linked.

In the present specification, a halogen group is fluorine, chlorine, bromine, or iodine.

In the present specification, the alkyl group may be straight-chained, branched or cyclic, and the number of carbon atoms thereof is not particularly limited, but is preferably 1 to 40. According to an exemplary embodiment, the number of carbon atoms of the alkyl group is 1 to 20. Specific examples thereof include a methyl group, an ethyl group, a propyl group, a n-propyl group, an isopropyl group, a butyl group, a n-butyl group, an isobutyl group, a tert-butyl group, a sec-butyl group, a pentyl group, a n-pentyl group, an isopentyl group, a tert-pentyl group, a hexyl group, a n-hexyl group, a heptyl group, a n-heptyl group, a hexyl group, a n-hexyl group, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include a methoxy group, an ethoxy group, a n-propoxy group, an isopropoxy group, an i-propyloxy group, a n-butoxy group, an isobutoxy group, a tert-butoxy group, a sec-butoxy group, a n-pentyloxy group, a neopentyloxy group, an isopentyloxy group, a n-hexyloxy group, a 3,3-dimethylbutyloxy group, a 2-ethylbutyloxy group, a n-octyloxy group, a n-nonyloxy group, a n-decyloxy group, a benzyloxy group, a p-methylbenzyloxy group, and the like, but are not limited thereto.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 40. According to an exemplary embodiment, the number of carbon atoms of the aryl group is 6 to 20. Examples of a monocyclic aryl group as the aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

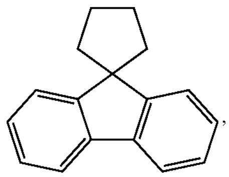,
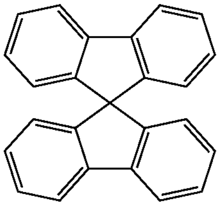

(spirofluorene),

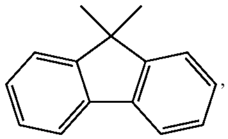,
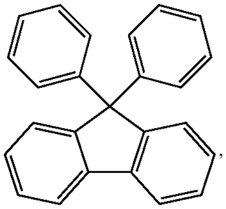, and the like. However, the substituent is not limited thereto.

In the present specification, a heteroaryl group includes one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 60. According to an exemplary embodiment, the number of carbon atoms of the heteroaryl group is 2 to 40. According to an exemplary embodiment, the number of carbon atoms of the heteroaryl group is 2 to 20. The heteroaryl group may be monocyclic or polycyclic. Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the alkylene group may be selected from the above-described examples of the alkyl group, except for being a divalent group.

In an exemplary embodiment of the present specification, R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group.

In an exemplary embodiment of the present specification, R1 to R6 are the same as or different from each other, and are each independently hydrogen; deuterium; a halogen group; a substituted or unsubstituted alkyl group; a substituted or unsubstituted aryl group; or a substituted or unsubstituted heteroaryl group.

In an exemplary embodiment of the present specification, R1 to R6 are the same as or different from each other, and are each independently hydrogen; deuterium; a halogen group; a substituted or unsubstituted alkyl group having 1 to 40 carbon atoms; a substituted or unsubstituted aryl group having 6 to 60 carbon atoms; or a substituted or unsubstituted heteroaryl group having 2 to 60 carbon atoms.

In an exemplary embodiment of the present specification, R1 to R6 are the same as or different from each other, and are each independently hydrogen; deuterium; a halogen group; or a substituted or unsubstituted alkyl group having 1 to 20 carbon atoms.

In an exemplary embodiment of the present specification, R1 to R6 are the same as or different from each other, and are each independently hydrogen; deuterium; a halogen group; a substituted or unsubstituted methyl group; a substituted or unsubstituted ethyl group; a substituted or unsubstituted propyl group; a substituted or unsubstituted butyl group; a substituted or unsubstituted isobutyl group; a substituted or unsubstituted tert-butyl group; a substituted or unsubstituted pentyl group; or a substituted or unsubstituted hexyl group.

In an exemplary embodiment of the present specification, R1 to R6 are the same as or different from each other, and are each independently hydrogen; deuterium; a halogen group; a methyl group which is unsubstituted or substituted with a halogen group; an ethyl group which is unsubstituted or substituted with a halogen group; a propyl group which is unsubstituted or substituted with a halogen group; a substituted or unsubstituted butyl group; an isobutyl group which is unsubstituted or substituted with a halogen group; a tert-butyl group which is unsubstituted or substituted with a halogen group; a pentyl group which is unsubstituted or substituted with a halogen group; or a hexyl group which is unsubstituted or substituted with a halogen group.

In an exemplary embodiment of the present specification, R1 to R6 are the same as or different from each other, and are each independently hydrogen; deuterium; fluorine; a methyl group which is unsubstituted or substituted with fluorine; an ethyl group; a propyl group; a butyl group; an isobutyl group; a tert-butyl group; a pentyl group; or a hexyl group.

In an exemplary embodiment of the present specification, R1 to R6 are the same as or different from each other, and are each independently hydrogen; or a substituted or unsubstituted alkyl group having 1 to 30 carbon atoms.

In an exemplary embodiment of the present specification, R1 to R6 are the same as or different from each other, and are each independently hydrogen; or a substituted or unsubstituted alkyl group having 1 to 30 carbon atoms, which is unsubstituted or substituted with a halogen group.

In an exemplary embodiment of the present specification, R1 to R6 are the same as or different from each other, and are each independently hydrogen; a methyl group which is unsubstituted or substituted with fluorine; or a tert-butyl group.

In an exemplary embodiment of the present specification, R1 and R6 are the same as or different from each other, and are each independently hydrogen; a methyl group which is unsubstituted or substituted with fluorine; or a tert-butyl group.

In an exemplary embodiment of the present specification, R2 to R5 are hydrogen.

In an exemplary embodiment of the present specification, n1 and n6 are the same as or different from each other, and are each independently an integer from 0 to 2.

In an exemplary embodiment of the present specification, Ar1 and Ar2 are the same as or different from each other, and are each independently a substituted or unsubstituted aryl group having 6 to 60 carbon atoms; or a substituted or unsubstituted heteroaryl group having 2 to 60 carbon atoms.

In another exemplary embodiment, Ar1 and Ar2 are the same as or different from each other, and are each independently a substituted or unsubstituted aryl group having 6 to 40 carbon atoms; or a substituted or unsubstituted heteroaryl group having 2 to 40 carbon atoms.

In still another exemplary embodiment, Ar1 and Ar2 are the same as or different from each other, and are each independently a substituted or unsubstituted aryl group having 6 to 30 carbon atoms.

According to an exemplary embodiment of the present specification, Ar1 and Ar2 are the same as or different from each other, and are each independently a substituted or unsubstituted phenyl group; a substituted or unsubstituted biphenyl group; a substituted or unsubstituted naphthyl group; a substituted or unsubstituted fluorenyl group.

In an exemplary embodiment of the present specification, Ar1 and Ar2 are the same as or different from each other, and are each independently a phenyl group which is unsubstituted or substituted with deuterium or an alkyl group; a biphenyl group which is unsubstituted or substituted with deuterium or an alkyl group; a naphthyl group which is unsubstituted or substituted with deuterium or an alkyl group; a fluorenyl group which is unsubstituted or substituted with deuterium or an alkyl group.

In another exemplary embodiment, Ar1 and Ar2 are the same as or different from each other, and are each independently a phenyl group; a biphenyl group; or a naphthyl group.

In an exemplary embodiment of the present specification, Ar1 and Ar2 may be any one of the following structures, but are not limited thereto, and the following structures may be additionally substituted.

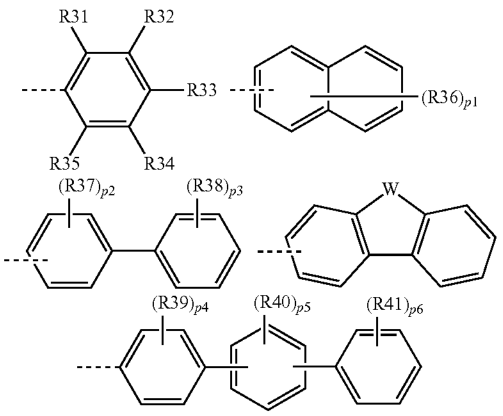

-continued

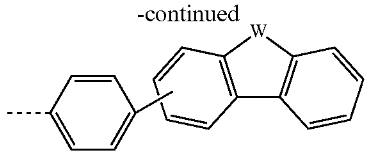

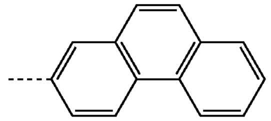

In the structures,

W is O, S, NRa, CRbRc or SiRdRe,

R31 to R41, Ra, Rb, Rc, Rd, and Re are the same as or different from each other, and are each independently hydrogen; deuterium; a halogen group; a substituted or unsubstituted alkyl group; or a substituted or unsubstituted aryl group, p1 is an integer from 0 to 7, p2, p4, and p5 are the same as or different from each other, and are each independently an integer from 0 to 4, p3 and p6 are the same as or different from each other, and are each independently an integer from 0 to 5, when p1 to p6 are each 2 or higher, each occurrence of R36 to R41 is the same as or different from each other, and ------ is a moiety bonded to Chemical Formula 1.

In an exemplary embodiment of the present specification, R31 to R41 are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In an exemplary embodiment of the present specification, R31 to R41 are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, R31 to R41 are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

In still another exemplary embodiment, R31 to R41 are each hydrogen.

In an exemplary embodiment of the present specification, W is O.

In an exemplary embodiment of the present specification, W is S.

In an exemplary embodiment of the present specification, W is CRbRc.

In an exemplary embodiment of the present specification, W is SiRdRe.

In an exemplary embodiment of the present specification, Rb, Rc, Rd, and Re are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In an exemplary embodiment of the present specification, Rb, Rc, Rd, and Re are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In an exemplary embodiment of the present specification, Rb, Rc, Rd, and Re are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

In an exemplary embodiment of the present specification, Rb, Rc, Rd, and Re are the same as or different from each other, and are each independently hydrogen; deuterium; a substituted or unsubstituted methyl group; a substituted or unsubstituted ethyl group; or a substituted or unsubstituted phenyl group.

In an exemplary embodiment of the present specification, Rb, Rc, Rd, and Re are the same as or different from each other, and are each independently hydrogen; deuterium; a methyl group; an ethyl group; or a phenyl group.

In an exemplary embodiment of the present specification, X1 and X2 are the same as or different from each other, and are each independently hydrogen; or a halogen group, and at least one of X1 and X2 is a halogen group.

In an exemplary embodiment of the present specification, X1 is a halogen group, and X2 is hydrogen.

In an exemplary embodiment of the present specification, X1 is fluorine, and X2 is hydrogen.

In an exemplary embodiment of the present specification, X1 is hydrogen, and X2 is a halogen group.

In an exemplary embodiment of the present specification, X1 is hydrogen, and X2 is fluorine.

In an exemplary embodiment of the present specification, X1 and X2 are each fluorine.

When L1 is a direct bond, the number 9 carbon of fluorene is directly bonded to X3, and a specific structure thereof is as follows.

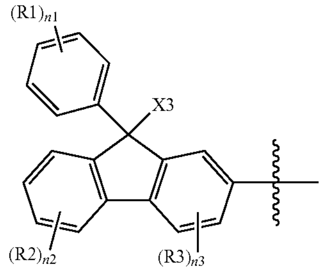

When L2 is a direct bond, the number 9 carbon of fluorene is directly bonded to X4, and a specific structure thereof is as follows.

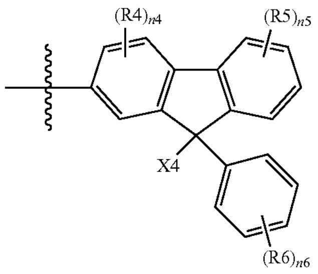

In an exemplary embodiment of the present specification, X3 and X4 are the same as or different from each other, and are each independently a photocurable group or a thermosetting group.

When X3 and X4 are a photocurable group or a thermosetting group, there is an advantage in that a solution process can be performed when the compound is applied to an organic light emitting device.

For example, in the forming of the organic material layer by using the compound, a plurality of fluorene-based compounds form a cross-linkage by a heat treatment or a light treatment, so that it is possible to provide an organic material layer including a thin filmed structure. Further, it is possible to prevent the organic material layer from being dissolved, morphologically affected or decomposed by a solvent when another layer is stacked on the surface of the formed organic material layer.

In an exemplary embodiment of the present specification, X3 and X4 are the same as or different from each other, and are each independently a photocurable group or a thermosetting group, and may have the following structure.

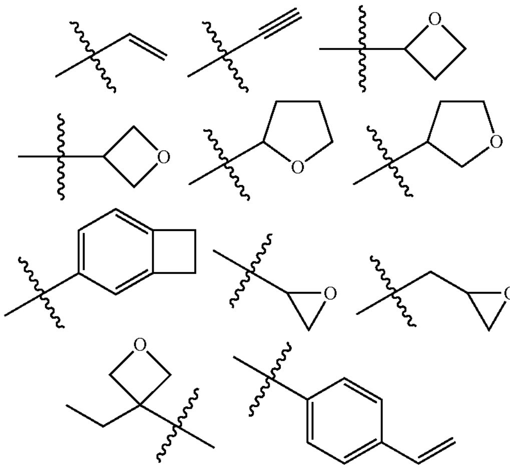

In an exemplary embodiment of the present specification, X3 and X4 are

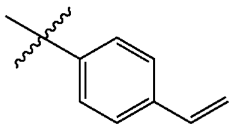

or

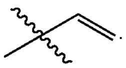

In an exemplary embodiment of the present specification, m1 and m2 are each 1.

In an exemplary embodiment of the present specification, Chemical Formula 1 is represented by the following Chemical Formula 1-1.

[Chemical Formula 1-1]

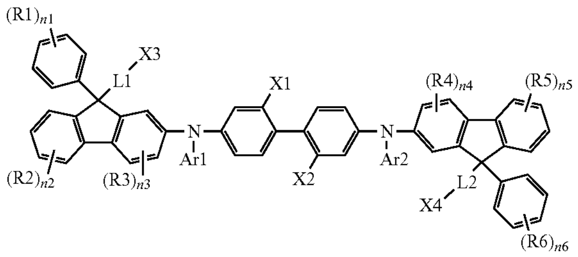

In Chemical Formula 1-1, X1 to X4, L1, L2, R1 to R6, Ar1, Ar2, and n1 to n6 are the same as those defined in Chemical Formula 1.

The compound represented by Chemical Formula 1-1 can be easily polymerized by specifying the positions of X1 and X2.

In an exemplary embodiment of the present specification, the fluorene-based compound of Chemical Formula 1 may be represented by any one of the following structures.

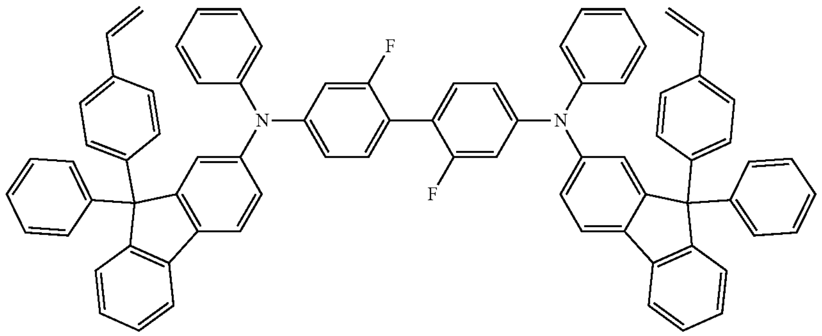

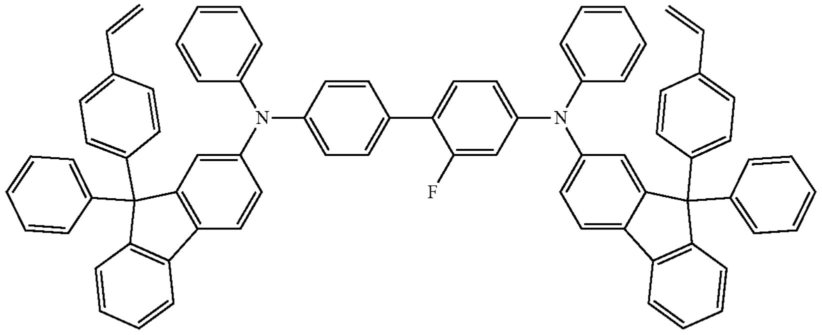

-continued
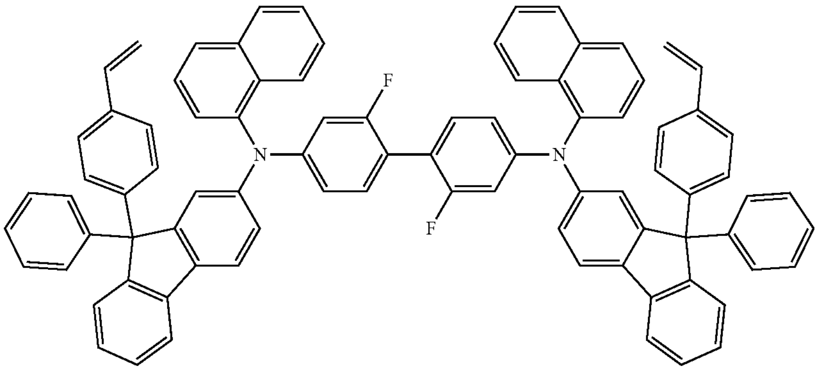
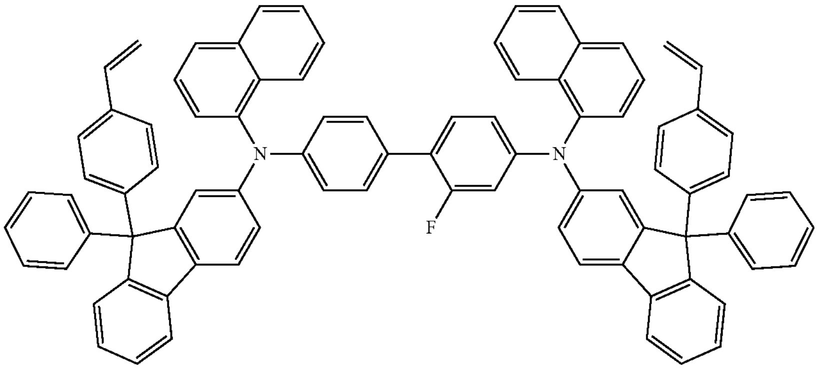
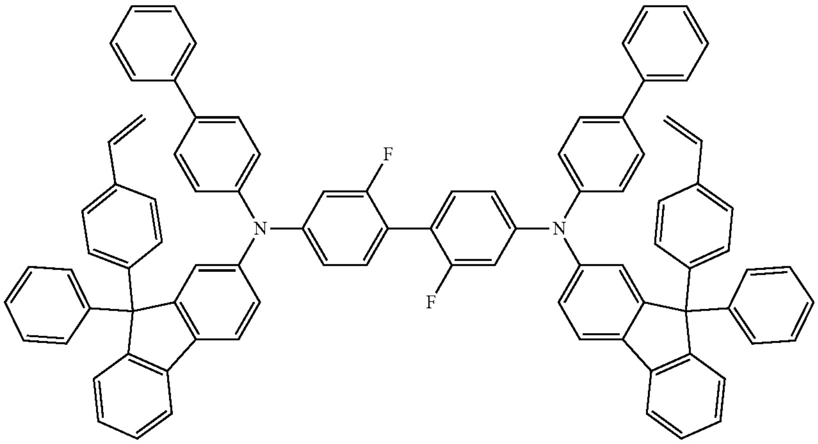
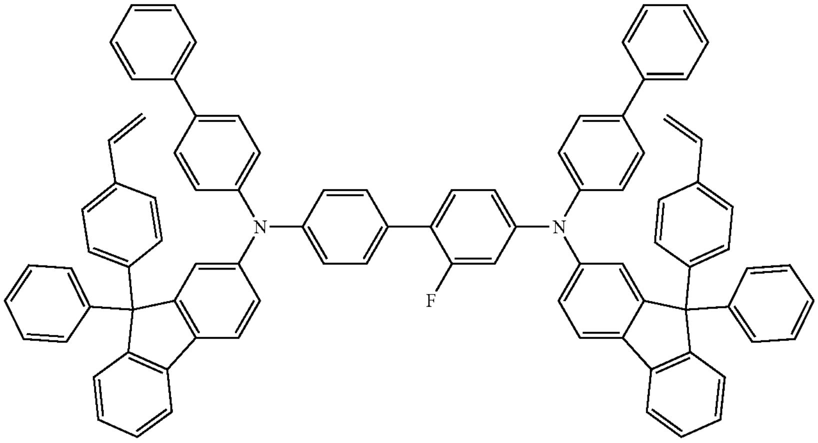

-continued
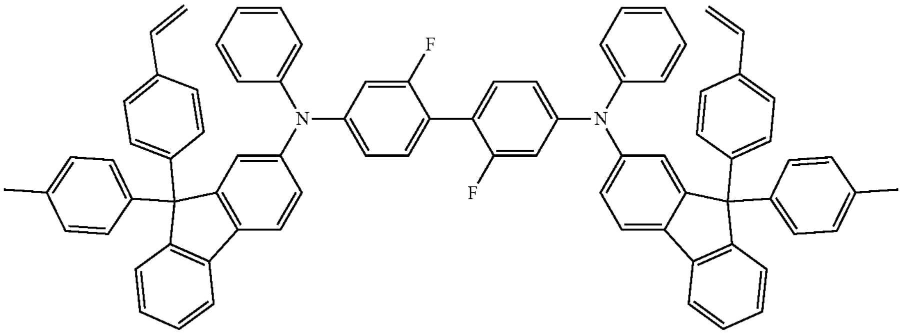
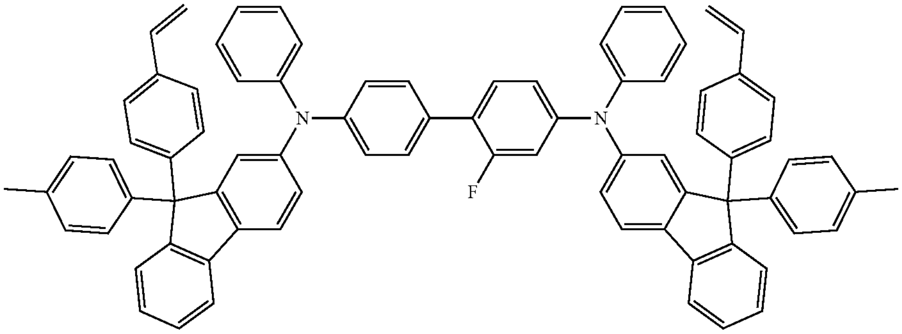
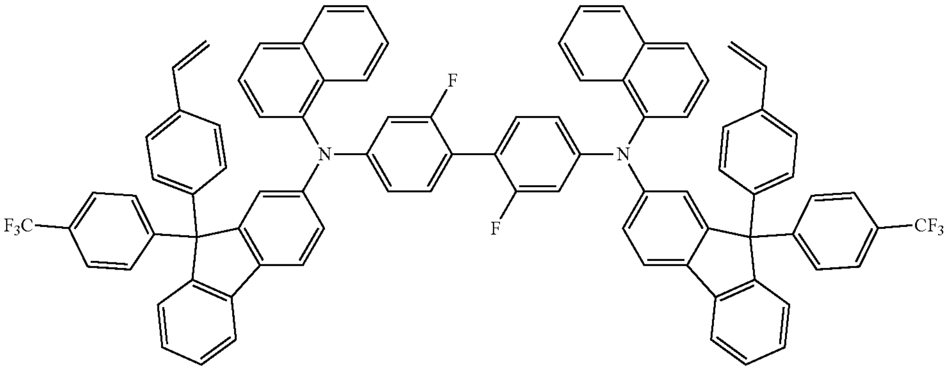
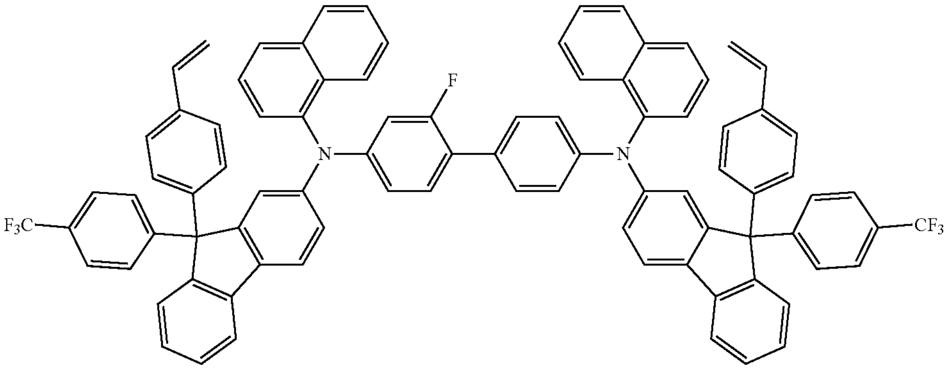

-continued
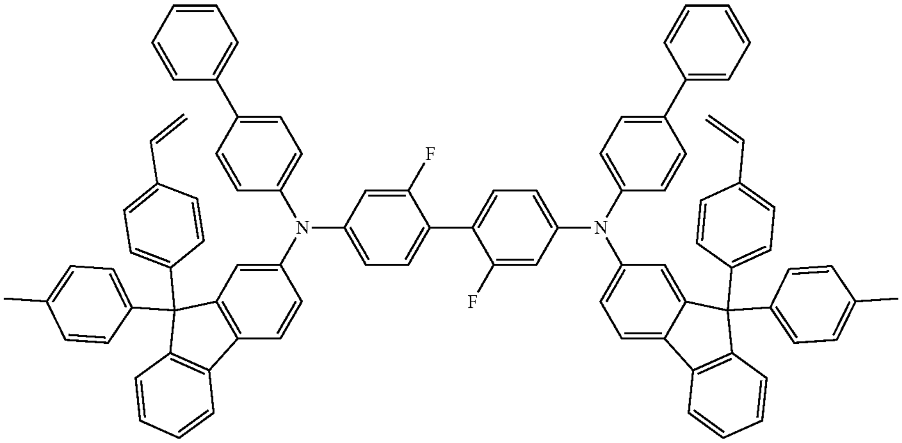
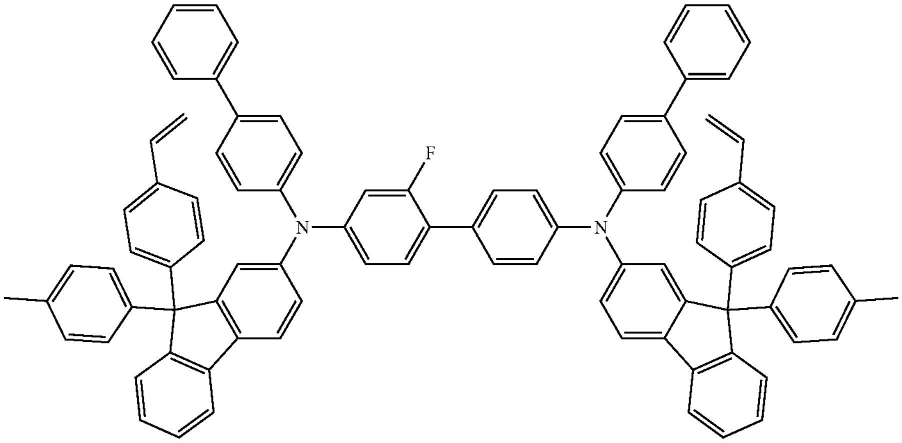
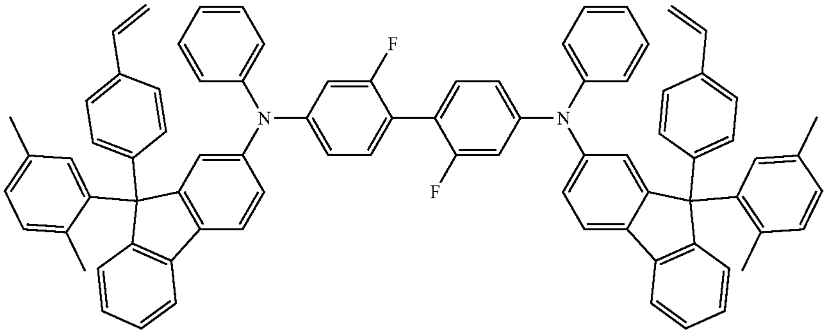
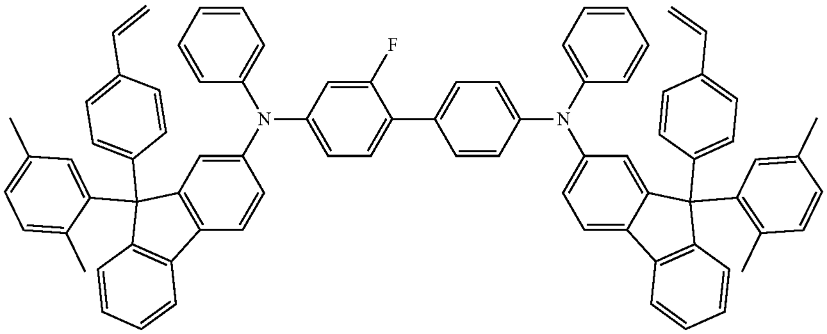

-continued
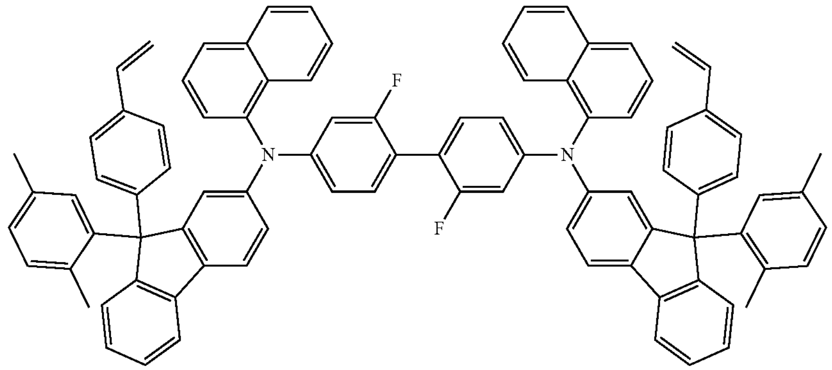
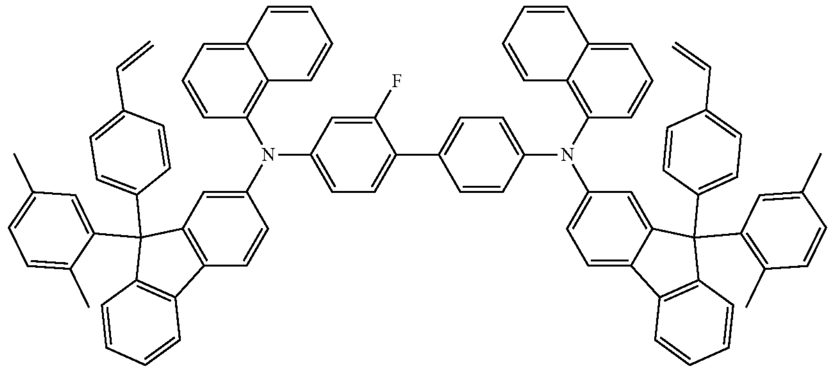
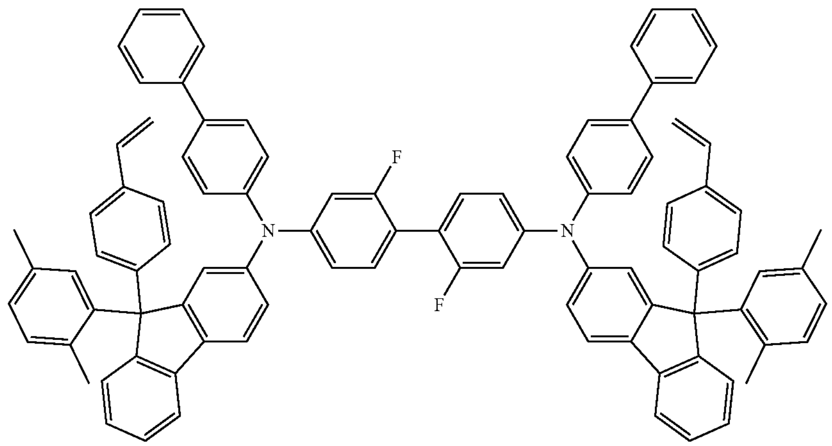
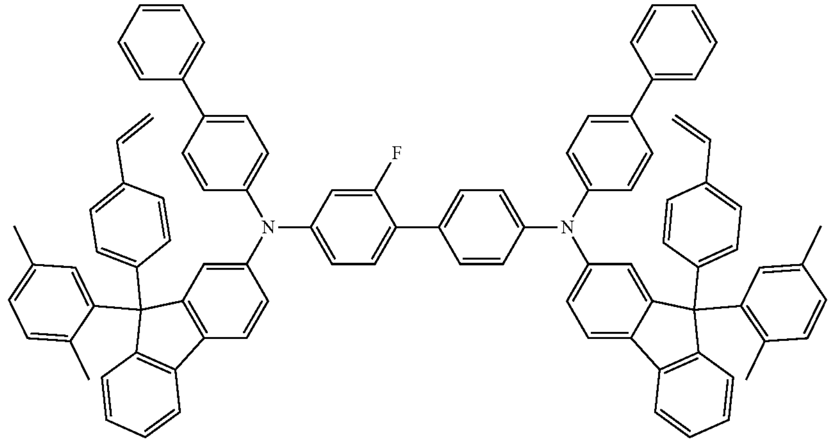

-continued
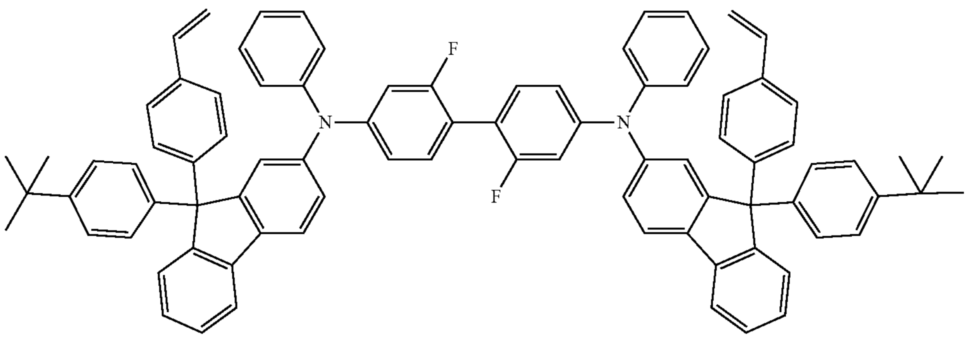
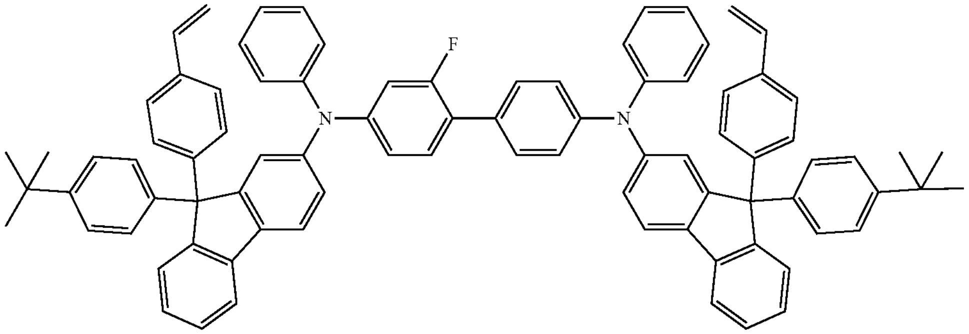
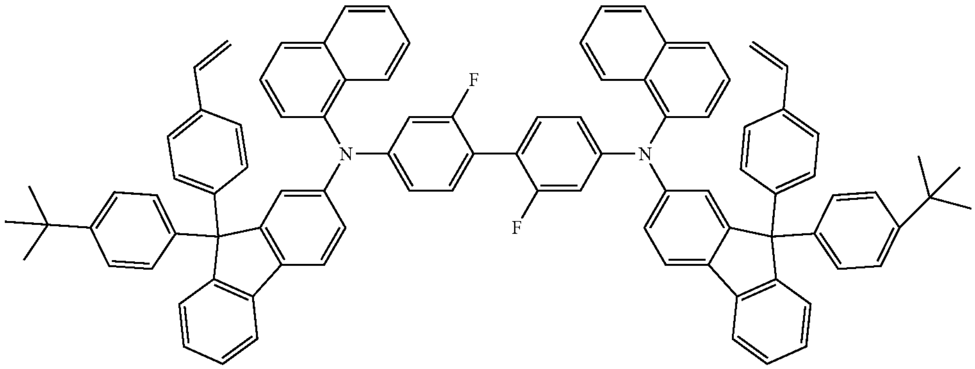
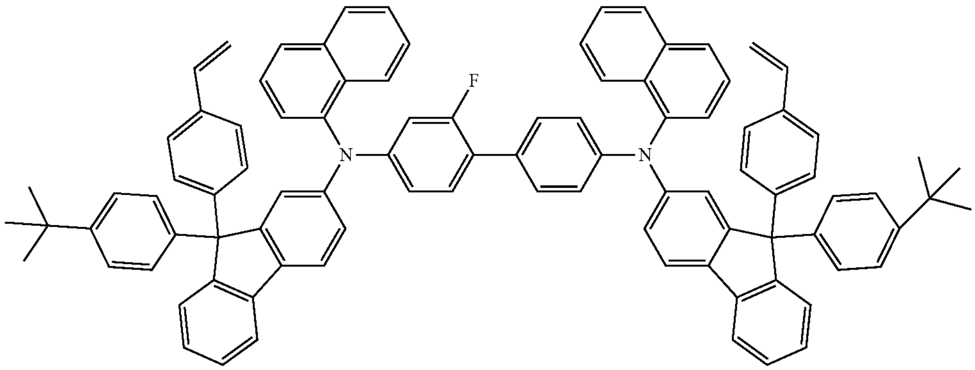

-continued

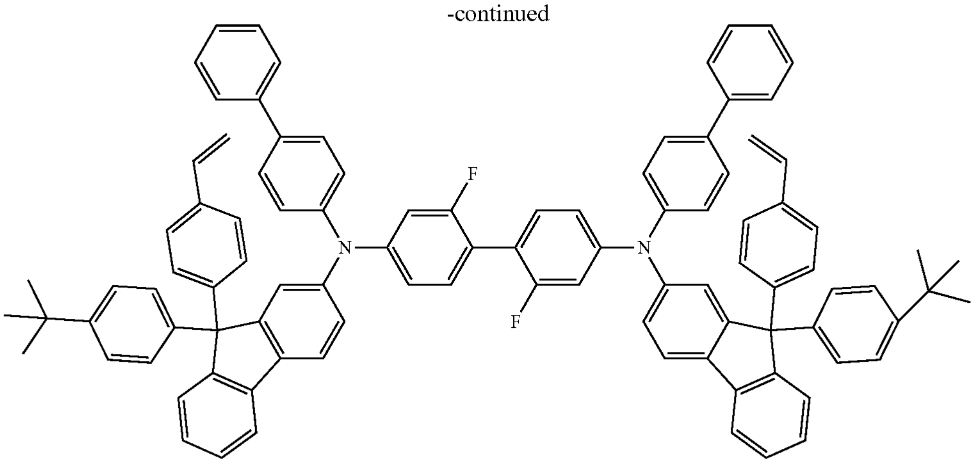

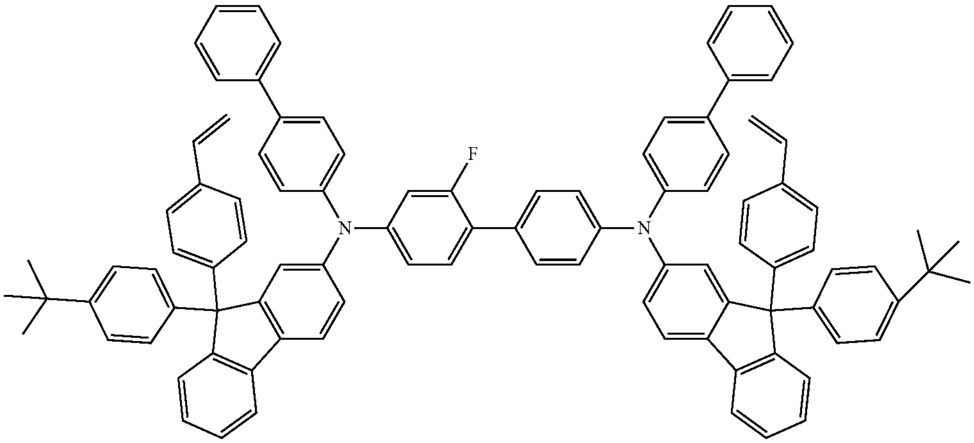

The fluorene-based compound according to an exemplary embodiment of the present specification may be prepared by a preparation method to be described below.

For example, for the fluorene-based compound of Chemical Formula 1, a core structure may be prepared by the following preparation method. In this case, the substituent may be bonded by a method known in the art, and the type and position of the substituent or the number of substituents may be changed according to the technology known in the art.

<General Preparation Method of Chemical Formula 1>

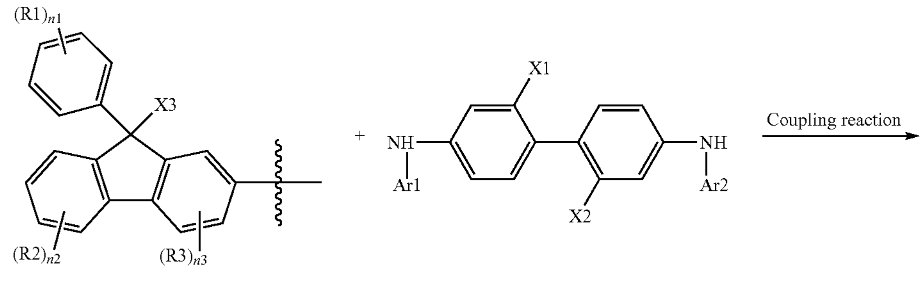

-continued

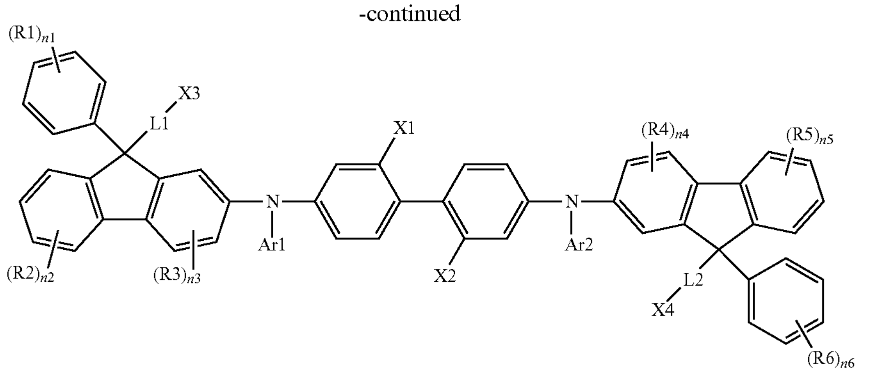

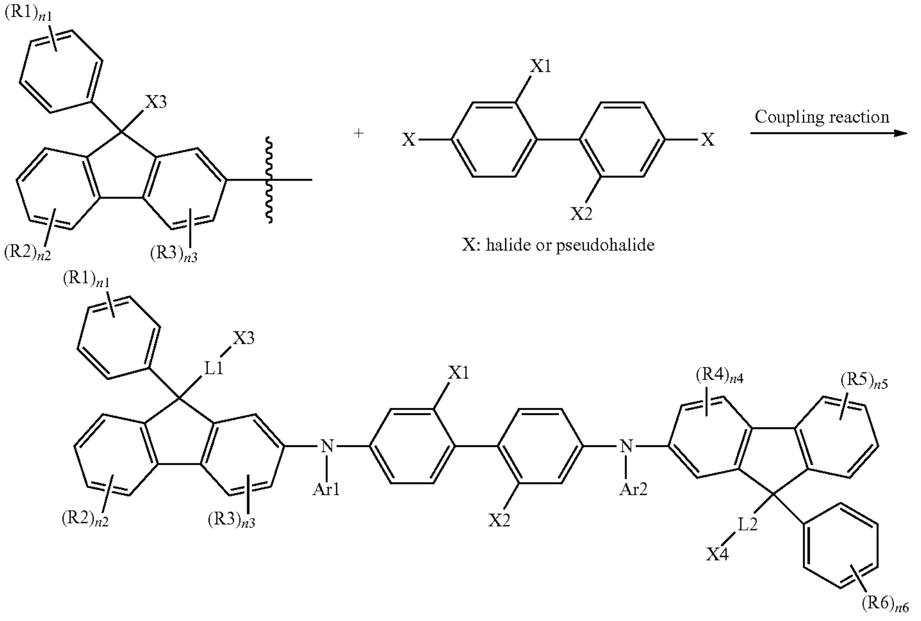

The substituents of the preparation method are the same as the definition of the substituents of Chemical Formula 1.

An exemplary embodiment of the present specification provides a coating composition including the above-described fluorene-based compound.

In an exemplary embodiment of the present specification, the coating composition includes the fluorene-based compound and a solvent.

In an exemplary embodiment of the present specification, the coating composition may be in a liquid phase. The "liquid phase" means that the composition is in a liquid state at room temperature under atmospheric pressure.

In an exemplary embodiment of the present specification, the above-described fluorene-based compound has solubility for some solvents.

In an exemplary embodiment of the present specification, the solvent may be, for example, a chlorine-based solvent such as chloroform, methylene chloride, 1,2-dichloroethane, 1,1,2-trichloroethane, chlorobenzene, and o-dichlorobenzene; an ether-based solvent such as tetrahydrofuran and dioxane; an aromatic hydrocarbon-based solvent such as toluene, xylene, trimethylbenzene, and mesitylene; an aliphatic hydrocarbon-based solvent such as cyclohexane, methylcyclohexane, n-pentane, n-hexane, n-heptane, n-octane, n-nonane, and n-decane; a ketone-based solvent such as acetone, methyl ethyl ketone, cyclohexanone, isophorone, tetralone, decalone, and acetylacetone; an ester-based solvent such as ethyl acetate, butyl acetate, and ethyl cellosolve acetate; a polyhydric alcohol such as ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, and 1,2-hexanediol, and derivatives thereof; an alcohol-based solvent such as methanol, ethanol, propanol, isopropanol, and cyclohexanol; a sulfoxide-based solvent such as dimethyl sulfoxide; an amide-based solvent such as N-methyl-2-pyrrolidone and N,N-dimethylformamide; and tetralin, but the solvent is sufficient as long as the solvent may dissolve or disperse the fluorene derivative according to an exemplary embodiment of the present invention, and is not limited thereto.

In an exemplary embodiment of the present specification, the solvents may be used either alone or in a mixture of two or more solvents.

In an exemplary embodiment of the present specification, as a result of measuring the fluorene-based compound of Chemical Formula 1 by a differential scanning calorimeter (DSC), a difference in temperature between an exothermic peak and an endothermic peak before the exothermic peak is 20° C. or more. Specifically, the difference in temperature between the exothermic peak and the endothermic peak before the exothermic peak may be 20° C. to 200° C.

The differential scanning calorimeter (DSC) means a device which can quantitatively measure variables such as a change in enthalpy of a sample to heat based on a qualitative analysis of the sample and a change in area of a peak during the denaturalization of the sample from positions, shapes, and the number of peaks obtained by showing a flow of heat as a function of temperature from the measurement of an amount of energy (enthalpy) required to maintain the difference in temperature between the sample and a reference material as zero while changing the temperatures of the sample and the reference material at a predetermined rate by a program.

In an exemplary embodiment of the present specification, the coating composition does not further include a p-doping material.

In an exemplary embodiment of the present specification, the coating composition further includes a p-doping material.

In the present specification, the p-doping material means a material which allows a host material to have p-semiconductor characteristics. The p-semiconductor characteristics mean characteristics of injecting or transporting holes at the highest occupied molecular orbital (HOMO) energy level, that is, characteristics of a material having large hole conductivity.

In an exemplary embodiment of the present specification, the p-doping material is sufficient as long as the material is a material which allows a host material to have p-semiconductor characteristics, one or two or more thereof may be used, and the type thereof is not limited.

Examples of the p-doping material are F4TCNQ; or a compound including a boron anion. Specifically, examples of the p-doping material include any one of the following Chemical Formulae 9-1 to 9-3 or a Farylborate-based compound, but are not limited thereto.

[Chemical Formula 9-1]

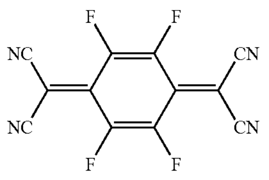

[Chemical Formula 9-2]

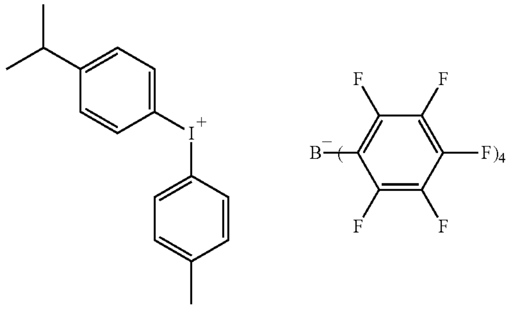

[Chemical Formula 9-3]

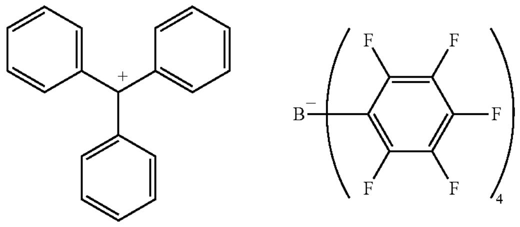

In an exemplary embodiment of the present specification, the content of the p-doping material is 0 wt % to 50 wt % based on the fluorene-based compound of Chemical Formula 1.

In an exemplary embodiment of the present specification, the content of the p-doping material is 0 wt % to 30 wt % based on the total solid content of the coating composition. In an exemplary embodiment of the present specification, it is preferred that the content of the p-doping material is 1 wt % to 30 wt % based on the total solid content of the coating composition, and in another exemplary embodiment, it is more preferred that the content of the p-doping material is 10 wt % to 30 wt % based on the total solid content of the coating composition.

In an exemplary embodiment of the present specification, the coating composition may further include: a single molecule including a thermosetting group or a photocurable group; or a single molecule including an end group capable of forming a polymer by heat.

In an exemplary embodiment of the present specification, the single molecule including a thermosetting group or a photocurable group; or the single molecule including an end group capable of forming a polymer by heat may be a compound having a molecular weight of 2,000 g/mol or less.

In an exemplary embodiment of the present specification, the coating composition further includes: a single molecule having a molecular weight of 2,000 g/mol or less while including a thermosetting group or a photocurable group; or a single molecule including an end group capable of forming a polymer by heat.

In an exemplary embodiment of the present specification, the single molecule including a thermosetting group or a photocurable group is an aryl such as phenyl, biphenyl, fluorene, and naphthalene; arylamine; or fluorene, and the single molecule including an end group capable of forming a polymer by heat may mean a single molecule in which an end group capable of forming a polymer by heat is substituted.

In an exemplary embodiment of the present specification, the coating composition may further include one or two compounds selected from the group consisting of a compound, in which a thermosetting group or a photocurable group is introduced into the molecule, and a polymer compound.

In an exemplary embodiment of the present specification, the coating composition may further include a compound in which a thermosetting group or a photocurable group is introduced into the molecule. When the coating composition further includes a compound in which a thermosetting group or a photocurable group is introduced into the molecule, a cure degree of the coating composition may be further increased.

In an exemplary embodiment of the present specification, the compound in which a thermosetting group or a photocurable group is introduced into the molecule has a molecular weight of 1,000 g/mol to 3,000 g/mol.

In an exemplary embodiment of the present specification, the coating composition may further include a polymer compound. When the coating composition further includes a polymer compound, the ink characteristic of the coating composition may be enhanced. That is, a coating composition further including the polymer compound may provide a viscosity suitable for coating or inkjet printing.

In an exemplary embodiment of the present specification, the coating composition may further include one or two or more additives selected from the group consisting of a thermal polymerization initiator and a photopolymerization initiator.

In an exemplary embodiment of the present specification, the coating composition has a viscosity of 2 cP to 15 cP.

In an exemplary embodiment of the present specification, the coating composition has a thin film retention rate of 95% or more in a thin film retention test, after a heat treatment at 250° C. or less. The coating composition of the present invention has excellent resistance to a solvent such as toluene and cyclohexanone because the thin film retention rate in the thin film retention test is 95% or more after the heat treatment at 250° C. or less.

In the thin film retention test, a thin film is first formed by spin-coating the coating composition onto a substrate (for example, glass, and the like), a heat treatment is performed in a nitrogen atmosphere, and then UV absorbance of the thin film is measured. Thereafter, the thin film retention rate is measured by dipping the thin film into a solvent such as toluene and cyclohexanone for about 10 minutes, drying the thin film, and then measuring UV absorbance of the thin film to compare the sizes of UV absorbance maximum peaks before and after dipping the thin film into the solvent (the size of the UV absorbance maximum peak after dipping the thin film into the solvent/the size of the UV absorbance maximum peak before dipping the thin film into the solvent×100).

An exemplary embodiment of the present specification provides an organic light emitting device formed by using the coating composition.

An exemplary embodiment of the present specification provides an organic light emitting device including: a first electrode;

a second electrode; and an organic material layer having one or more layers provided between the first electrode and the second electrode, in which one or more layers of the organic material layer include the coating composition or a cured product thereof, and the cured product of the coating composition is in a state in which the coating composition is cured by a heat treatment or a light treatment.

In the present specification, the cured product means a state in which a photocurable group or a thermosetting group included in the compound is bonded to another material and/or the compound included in the layer to which the compound is applied. For example, when the photocurable group or the thermosetting group includes a double bond, it may mean that the double bond is changed to a single bond and converted into a polymerized state between the compounds.

In an exemplary embodiment of the present specification, the organic material layer including the coating composition or the cured product thereof is a hole transport layer, a hole injection layer, or a layer which simultaneously transports and injects holes.

In an exemplary embodiment of the present specification, the organic material layer including the coating composition or the cured product thereof is a hole injection layer.

In another exemplary embodiment, the organic material layer including the coating composition or the cured product thereof is a light emitting layer.

In still another exemplary embodiment, the organic material layer including the coating composition or the cured product thereof is a light emitting layer, and the light emitting layer includes the fluorene-based compound as a host of the light emitting layer.

In an exemplary embodiment of the present specification, the organic light emitting device further includes one or two or more layers selected from the group consisting of a hole injection layer, a hole transport layer, an electron transport layer, an electron injection layer, an electron blocking layer, and a hole blocking layer.

In an exemplary embodiment of the present specification, the first electrode is an anode, and the second electrode is a cathode.

According to another exemplary embodiment, the first electrode is a cathode, and the second electrode is an anode.

In another exemplary embodiment, the organic light emitting device may be a normal type organic light emitting device in which an anode, an organic material layer having one or more layers, and a cathode are sequentially stacked on a substrate.

In still another exemplary embodiment, the organic light emitting device may be an inverted type organic light emitting device in which a cathode, an organic material layer having one or more layers, and an anode are sequentially stacked on a substrate.

The organic material layer of the organic light emitting device of the present specification may also be composed of a single-layered structure, but may be composed of a multi-layered structure in which an organic material layer having two or more layers is stacked. For example, the organic light emitting device of the present invention may have a structure including two or more layers among a hole injection layer, a hole transport layer, a layer which simultaneously injects and transports holes, a light emitting layer, an electron transport layer, an electron injection layer, and a layer which simultaneously injects and transport electrons, as an organic material layer. However, the structure of the organic light emitting device is not limited thereto, and may include a fewer number of organic layers.

The organic light emitting device of the present specification may be stacked in order of [a substrate/an anode/a hole injection layer/a hole transport layer/a light emitting layer/an electron injection layer/an electron transport layer/a cathode].

In the organic light emitting device of the present specification according to another exemplary embodiment, [a substrate/an anode/a hole injection layer/a hole transport layer/a light emitting layer/an electron injection and transport layer/a cathode] may be stacked in this order.

The structure of the organic light emitting device according to an exemplary embodiment of the present specification is exemplified in FIG. 1.

FIG. 1 exemplifies a structure of an organic light emitting device in which an anode 201, a hole injection layer 301, a hole transport layer 401, a light emitting layer 501, an electron injection and transport layer 601, and a cathode 701 are sequentially stacked on a substrate 101.

However, the structure of the organic light emitting device of the present specification is not limited to FIG. 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layer are formed using a coating composition including the fluorene-based compound.

For example, the organic light emitting device of the present specification may be manufactured by sequentially stacking an anode, an organic material layer, and a cathode on a substrate. In this case, the organic light emitting device may be manufactured by depositing a metal or a metal oxide having conductivity, or an alloy thereof on a substrate to form an anode, forming an organic material layer including a hole injection layer, a hole transport layer, a light emitting layer, and an electron injection and transport layer thereon through a deposition or solution process, and then depositing a material, which may be used as a cathode, thereon, by using a physical vapor deposition (PVD) method such as sputtering or e-beam evaporation. In addition to the method described above, an organic light emitting device may be made by sequentially depositing a cathode material, an organic material layer, and an anode material on a substrate.

An exemplary embodiment of the present specification provides a method for manufacturing an organic light emitting device formed by using the coating composition.

Specifically, an exemplary embodiment of the present specification includes: preparing a substrate;

forming a first electrode on the substrate;

forming an organic material layer having one or more layers on the first electrode; and forming a second electrode on the organic material layer, in which the forming of the organic material layer includes forming an organic material layer having one or more layers by using the coating composition.

That is, one or more layers of the organic material layer are formed by using the coating composition.

In an exemplary embodiment of the present specification, the organic material layer formed by using the coating composition is formed by using a solution process.

In an exemplary embodiment of the present specification, the organic material layer formed by using the coating composition is formed by using spin coating.

In an exemplary embodiment of the present specification, the organic material layer formed by using the coating composition is formed by using a printing method.

Examples of the printing method include inkjet printing, nozzle printing, offset printing, transfer printing or screen printing, and the like, but are not limited thereto.

The coating composition according to an exemplary embodiment of the present specification is suitable for a solution process due to the structural characteristic thereof, so that the organic material layer may be formed by a printing method, and as a result, there is an economic effect in terms of time and costs when a device is manufactured.

In an exemplary embodiment of the present specification, the forming of the organic material layer formed by using the coating composition includes: coating the cathode or the anode with the coating composition; and heat-treating or light-treating the coated coating composition.

In an exemplary embodiment of the present specification, a heat treatment temperature in the heat-treating of the coating composition is 85° C. to 250° C.

In another exemplary embodiment, a heat treatment time in the heat-treating of the coating composition may be 1 minute to 1 hour.

In an exemplary embodiment of the present specification, when the coating composition does not include an additive, it is preferred that a cross-linkage proceeds by performing a heat treatment at a temperature of 100° C. to 250° C., and it is more preferred that a cross-linkage proceeds at a temperature of 120° C. to 200° C.

When the forming of the organic material layer by using the coating composition includes the heat-treating or light-treating of the coating composition, a plurality of fluorene-based compounds included in the coating composition may form a cross-linkage, thereby providing an organic material layer including a thin-filmed structure. In this case, it is possible to prevent the organic material layer from being dissolved, morphologically affected or decomposed by a solvent when another layer is stacked on the surface of the organic material layer formed by using the coating composition.

Therefore, when the organic material layer is formed by a method including the heat-treating or light-treating of the coated coating composition, resistance to a solvent is increased, so that a plurality of layers may be formed by repeatedly performing solution deposition and cross-linking methods, and stability is increased, so that the service life characteristic of the device may be increased.

For example, even though a coating composition is prepared by using a solvent that dissolves the compound and an organic material layer is manufactured by a solution process, the organic material layer may have resistance to the same solvent when cured through heat treatment or light treatment. Therefore, when an organic material layer is formed by using the compound and then subjected to a heat treatment process, a solution process can be performed even when another organic material layer is applied. As an example, when the coating composition is applied to a hole transport layer, during the manufacture of an upper layer (a light emitting layer, and the like), the upper layer can also be introduced into the solution process by using a specific solvent to which the cured coating composition exhibits resistance.

In an exemplary embodiment of the present specification, the coating composition including the fluorene-based compound may use a coating composition which is dispersed by being mixed with a polymeric binder.

In an exemplary embodiment of the present specification, as the polymeric binder, those which do not extremely suppress charge transport are preferred, and those which are not strong in absorption to visible light are preferably used. As the polymeric binder, poly(N-vinylcarbazole), polyaniline, and derivatives thereof, polythiophene and derivatives thereof, poly(p-phenylene vinylene) and derivatives thereof, poly(2,5-thienylene vinylene) and derivatives thereof, polycarbonate, polyacrylate, polymethyl acrylate, polymethyl methacrylate, polystyrene, polyvinyl chloride, polysiloxane, and the like are exemplified.

In an exemplary embodiment of the present specification, in the organic material layer of the organic light emitting device, a fluorene-based compound may also be included alone, may also be included in a thin-filmed state in which a coating composition including the fluorene-based compound is heat-treated or light-treated, and may also be included as a copolymer in which the fluorene-based compound is mixed with another monomer. Further, the fluorene-based compound may also be included as a copolymer in which the fluorene-based compound is mixed with another polymer, and may also be included as a mixture. In this case, the copolymer in which the fluorene-based compound is mixed with another monomer may be formed by including another monomer in the coating composition, and the copolymer in which the fluorene-based compound is mixed with another polymer may be formed by including the another polymer in the coating composition.

In an exemplary embodiment of the present specification, as the anode material, materials having a high work function are usually preferred so as to facilitate the injection of holes into an organic material layer. Specific examples of the anode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SNO_2$:Sb; a conductive polymer such as poly(3-methylthiophene), poly[3,4-(ethylene-1,2-dioxy) thiophene] (PEDOT), polypyrrole, and polyaniline; and the like, but are not limited thereto.

As the cathode material, materials having a low work function are usually preferred so as to facilitate the injection of electrons into an organic material layer. Specific examples of the cathode material include: a metal such as barium, magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes from an electrode, and a hole injection material is preferably a compound which has a capability of transporting holes, and thus has an effect of injecting holes at an anode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the anode material and the HOMO of the neighboring organic material layer. Specific examples of the hole injection material include the compound represented by Chemical Formula 1, metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based electrically conductive polymers, and the like, but are not limited thereto.

The hole transport layer is a layer which accepts holes from a hole injection layer and transports the holes to a light emitting layer, and a hole transport material is suitably a material having high hole mobility which may accept holes from an anode or a hole injection layer and transfer the holes to a light emitting layer. Examples of the hole transport material include arylamine-based organic materials, conductive polymers, block copolymers having both conjugated portions and non-conjugated portions, and the like, but are not limited thereto. The hole transport material may be specifically arylamine-based organic materials, more specifically, a-NPD, but is not limited thereto.

The light emitting material is a material which may accept holes and electrons from a hole transport layer and an electron transport layer, respectively, and combine the holes and the electrons to emit light in a visible ray region, and is preferably a material having high quantum efficiency for fluorescence or phosphorescence. Specific examples thereof include: 8-hydroxy-quinoline aluminum complexes ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivatives include anthracene derivatives, pyrene derivatives, naphthalene derivatives, pentacene derivatives, phenanthrene compounds, fluoranthene compounds, and the like, and examples of the hetero ring-containing compounds include carbazole derivatives, dibenzofuran derivatives, ladder-type furan compounds, pyrimidine derivatives, and the like, but the examples thereof are not limited thereto.

Examples of the dopant material include aromatic amine derivatives, styrylamine compounds, boron complexes, fluoranthene compounds, metal complexes, and the like. Specifically, the aromatic amine derivative is a fused aromatic ring derivative having a substituted or unsubstituted arylamino group, and examples thereof include pyrene, anthracene, chrysene, periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include iridium complexes, platinum complexes, and the like, but are not limited thereto.

Specifically, the light emitting layer includes anthracene derivatives as a host, and may include a compound in which at least one arylvinyl group is substituted with a substituted or unsubstituted arylamine as a dopant, but the host and the dopant are not limited thereto.

The electron transport layer is a layer which accepts electrons from an electron injection layer and transports the electrons to a light emitting layer, and an electron transport material is suitably a material having high electron mobility which may proficiently accept electrons from a cathode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transport layer may be used with any desired cathode material, as used according to the related art. In particular, examples of an appropriate cathode material include a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, phenanthroline, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]

quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The electron injection and transport layer is a layer which simultaneously injects and transports electrons. As the electron injection and transport layer material, any material applicable to the electron injection layer and the electron transport layer can be used without limitation. For example, phenanthroline derivatives may be used, but the electron injection and transport layer material is not limited thereto.

The hole blocking layer is a layer which blocks holes from reaching a cathode, and may be generally formed under the same conditions as those of the hole injection layer. Specific examples thereof include oxadiazole derivatives or triazole derivatives, phenanthroline derivatives, BCP, aluminum complexes, and the like, but are not limited thereto.

The organic light emitting device according to the present specification may be a top emission type, a bottom emission type, or a dual emission type according to the materials to be used.

In an exemplary embodiment of the present specification, the fluorene-based compound may be included in an organic solar cell or an organic transistor in addition to the organic light emitting device.

MODE FOR INVENTION

Hereinafter, the present specification will be described in detail with reference to Examples for specifically describing the present specification. However, the Examples according to the present specification may be modified into various forms, and it is not to be interpreted that the scope of the present specification is limited to the Examples described below. The Examples of the present specification are provided to describe the present specification more completely to a person with ordinary skill in the art.

PREPARATION EXAMPLES

Synthesis Example 1

Preparation of Compound 1

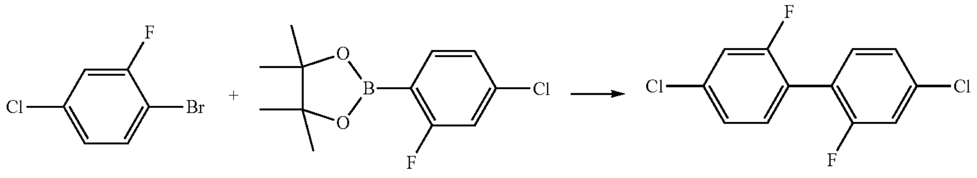

[A-1]

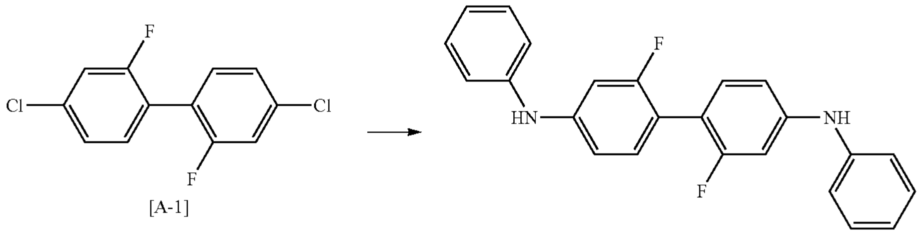

[A-1]

[B-1]

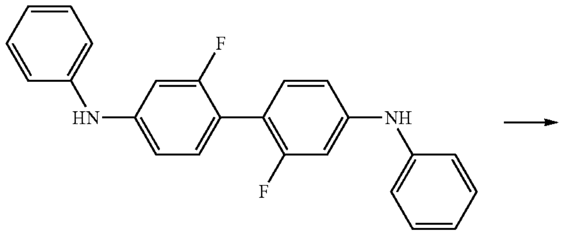

[B-1]

-continued

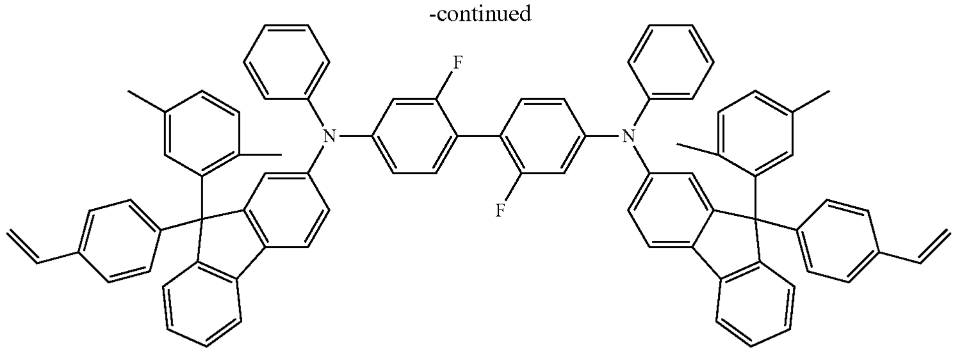

[1]

(1) Synthesis of Intermediate A-1

12.24 (1.3 eq) g of 1-bromo-4-chloro-2-fluorobenzene, 10 g (1.0 eq) of 2-(4-chloro-2-fluorophenyl)-4,4,5,5-tetramethyl-1,3,2-dioxaborolane, 0.13 g (0.005 eq) of $PdCl_2$ (AMPHOS), and 8.26 g (2.0 eq) of $Na_2CO_3$ were put into a round bottom flask and dissolved in 150 mL of toluene and 150 mL of $D_2O$. After the temperature was increased to 45° C., 1.57 g (0.10 eq) of Aliquit336 was injected thereinto. After stirring for 12 hours, the reaction was terminated with distilled water, an organic layer was extracted, and then 7.7 g of Intermediate A-1 of 100% purity was obtained with dichloromethane (DCM) and methanol.

FIG. 2 is a view illustrating NMR measurement results of Intermediate A-1.

(2) Synthesis of Intermediate B-1

7.7 g (1.0 eq) of Intermediate A-1, 6.9 g (2.2 eq) of aniline, 0.75 g (0.05 eq) of bis(tri-tert-butylphosphine)palladium(0) ($Pd_2$(t-Bu)P), and 7.14 g (2.5 eq) of sodium tert-butoxide (Na-t-butoxide) were put into a round bottom flask and dissolved in 200 mL of xylene. After the temperature was increased to 130° C., the solution was stirred for 12 hours. The reaction was terminated with distilled water, an organic layer was extracted, and then 8.0 g of Intermediate B-1 of 96% purity was obtained with dichloromethane (DCM) and hexane.

(3) Synthesis of Compound 1

After 2 g (1.0 eq) of Intermediate B-1 and 5.36 g (2.2 eq) of 2-bromo-9-(2,5-dimethylphenyl)-9-(4-vinylphenyl)-9H-fluorene were put into a round bottom flask and dissolved in 40 mL of toluene, 6.48 mL (2.5 eq) of 2.5 M sodium tert-pentoxide (Na-t-pentoxide) was slowly injected thereinto, and then 0.08 g (0.02 eq) of $Pd_2$(t-Bu)P was introduced thereinto, and the resulting mixture was stirred at 60° C. for 6 hours. The reaction was terminated with distilled water, an organic layer was extracted, and then 1 g of Compound 1 of 99.7% purity was obtained with THF and ethanol.

FIG. 3 illustrates HPLC measurement results of Compound 1.

HPLC was measured under the condition of THF: $H_2O$=60:40. Through the measured HPLC results, it was confirmed that the purity of Compound 1 was 99.7%.

Synthesis Example 2

Preparation of Compound 2

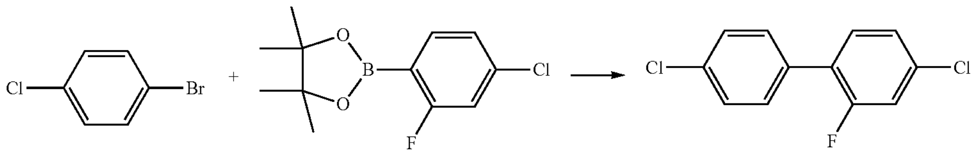

[A-2]

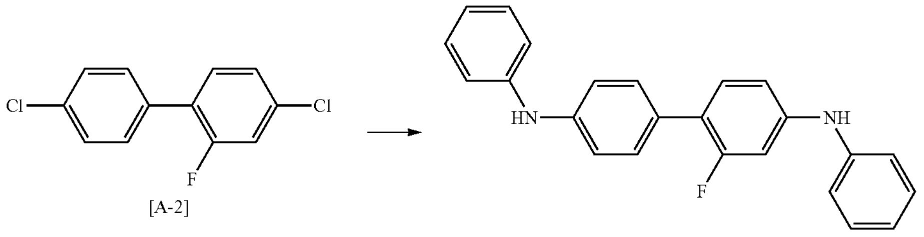

[A-2] [B-2]

-continued

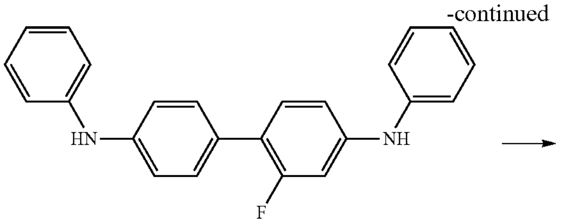

[B-2]

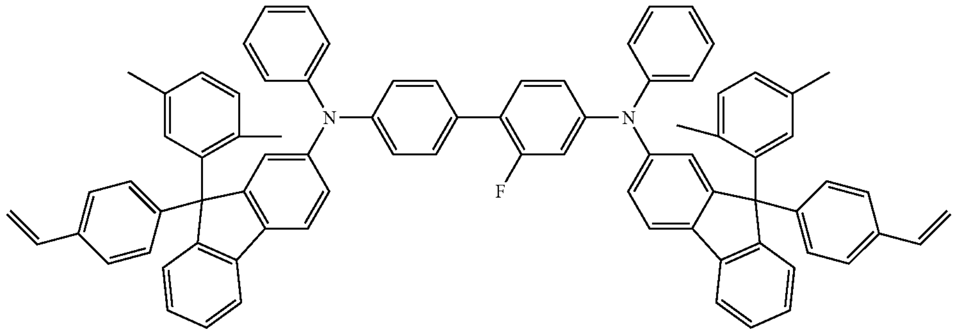

[2]

(1) Synthesis of Intermediate A-2

8.0 g of Intermediate A-2 of 100% purity was obtained in the same manner as in (1) of Preparation Example 1, except that 1-bromo-4-chlorobenzene was used instead of 1-bromo-4-chloro-2-fluorobenzene in (1) of Preparation Example 1.

(2) Synthesis of Intermediate B-2

8.0 g of Intermediate B-2 of 100% purity was obtained in the same manner as in (2) of Preparation Example 1, except that Intermediate A-2 was used instead of Intermediate A-1 in (2) of Preparation Example 1.

(3) Synthesis of Compound 2

1.0 g of Compound 2 of 99.7% purity was obtained in the same manner as in (3) of Preparation Example 1, except that Intermediate B-2 was used instead of Intermediate B-1 in (3) of Preparation Example 1.

Synthesis Example 3

Preparation of Compound 3

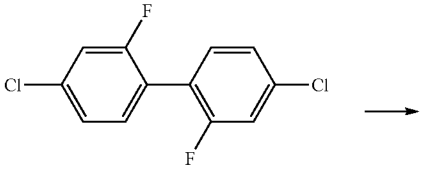

[A-1]

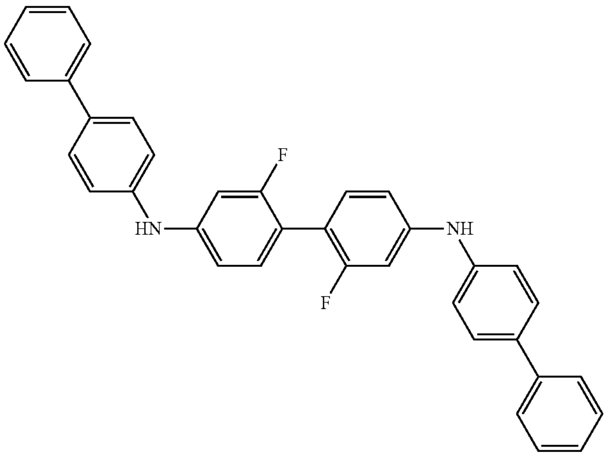

[B-3]

-continued

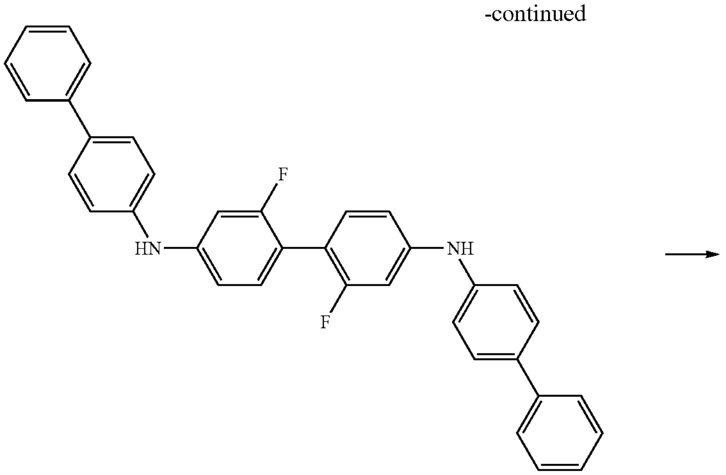

[B-3]

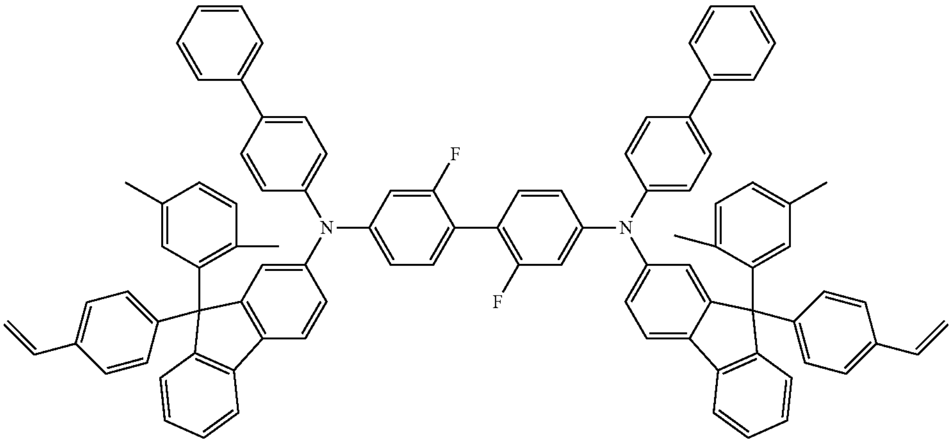

[3]

(1) Synthesis of Intermediate B-3

8.0 g of Intermediate B-3 of 100% purity was obtained in the same manner as in (2) of Preparation Example 1, except that bromo-biphenyl was used instead of aniline in (2) of Preparation Example 1.

(2) Synthesis of Compound 3

1.0 g of Compound 3 of 99.6% purity was obtained in the same manner as in (3) of Preparation Example 1, except that Intermediate B-3 was used instead of Intermediate B-1 in (3) of Preparation Example 1.

Experimental Example 1

Measurement of Thin Film Retention Rate

Coating Composition 1 was prepared by dissolving Compound 1 prepared in Synthesis Example 1 and a p-doping material of the following Chemical Formula 9-2 in toluene at a concentration of 2 wt % (Compound 1: Chemical Formula 9-2=8:2 (weight ratio)). Further, Coating Composition 2 was prepared by dissolving the following Comparative Compound 1 and the p-doping material of the following Chemical Formula 9-2 in toluene at a concentration of 2 wt % (Comparative Compound 1:Chemical Formula 9-2=8:2 (weight ratio)).

A thin film was formed by spin-coating Coating Compositions 1 and 2, respectively on glass. The thin film was heat-treated at 220° C. for 30 minutes, and UV absorbance was measured. The thin film was dipped again in toluene for 10 minutes and then dried, and UV absorbance was measured. From the comparison of sizes of the maximum peaks of UV absorbance before and after the dipping, the thin film retention rates could be confirmed.

[Chemical Formula 9-2]

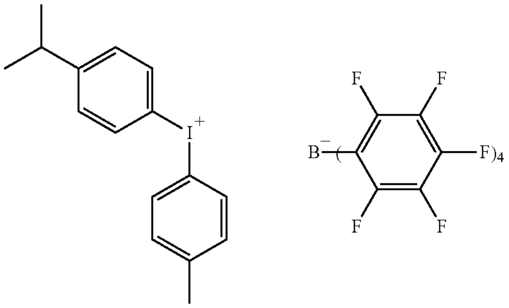

[Comparative Compound 1]

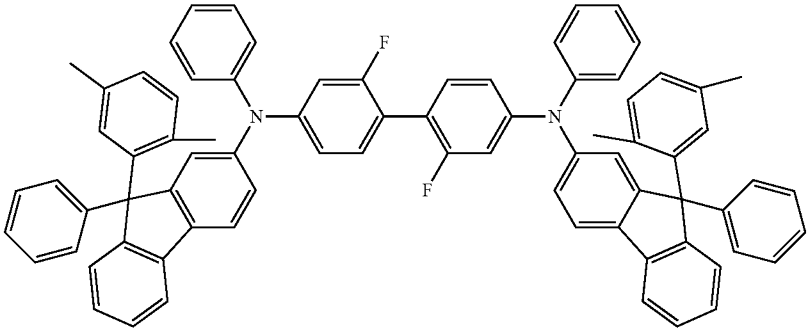

FIG. 4 is a view illustrating the film retention experimental results of a thin film formed by Coating Composition 1.

FIG. 5 is a view illustrating the film retention experimental results of a thin film formed by Coating Composition 2.

In FIGS. 4 and 5, the horizontal axis means the wavelength, the vertical axis means the optical density (OD), (a) is a UV measurement result immediately after the thin film is heat-treated (before being dipped in toluene for 10 minutes), and (b) is a UV measurement result after the thin film is dipped in toluene for 10 minutes.

Through FIG. 4, it can be confirmed that the thin film retention rate is 100% in the case of a thin film formed by Coating Composition 1 including the compound represented by Chemical Formula 1. In contrast, through FIG. 5, it can be confirmed that the thin film retention rate is 0% in the case of a thin film formed by Coating Composition 2 including Comparative Compound 1 which does not including a curable group.

Experimental Example 2

Measurement of Energy Level

A coating composition was prepared in which Compound 1 synthesized in Synthesis Example 1 and the following Comparative Compound 2 were each dissolved in toluene at a concentration of 2 wt %. A thin film was formed by spin-coating the coating composition on an ITO substrate. The energy level of the thin film formed with a thickness of about 30 nm was measured by an AC3 device, and the results are shown in the following Table 1.

TABLE 1

[Comparative Compound 2]

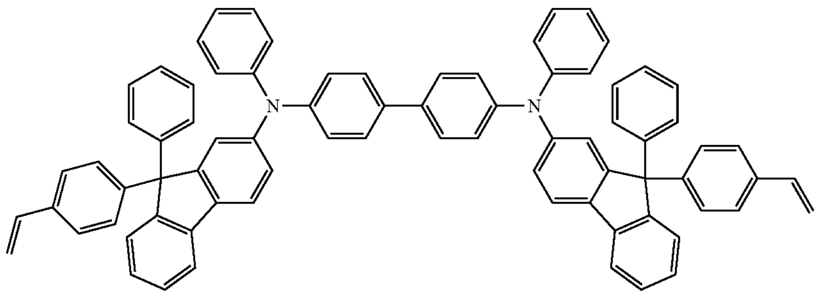

| | Comparative Compound 2 | Compound 1 |
|---|---|---|
| HOMO | 5.45 | 5.50 |
| LUMO | 2.44 | 2.40 |
| Band gap | 3.01 | 3.10 |

From Table 1, it can be confirmed that the HOMO energy level of Compound 1 into which F was introduced tended to be down-shifted compared to Comparative Compound 2 due to the electron withdrawing effect. In addition, F-introduced Compound 1 shows a larger bandgap than Comparative Compound 2, this brings about a synergistic effect of triplet state. Therefore, it can be confirmed that smoother hole movement may be formed when Compound 1 is applied at the time of manufacturing the device than when Comparative Compound 2 is applied.

Experimental Example 3

Manufacture of Organic Light Emitting Device

Example 1

A glass substrate thinly coated with indium tin oxide (ITO) to have a thickness of 1,500 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes.

After the washing with distilled water was completed, the substrate was ultrasonically washed with isopropyl alcohol and acetone solvents, and dried, and then the substrate was cleaned for 5 minutes, and the substrate was transported to a glovebox.

A coating composition in which Compound 1 and the p-doping material of Chemical Formula 9-2 were dissolved in toluene at a concentration of 1.5 wt % (Compound 1: Chemical Formula 9-2=8:2 (weight ratio)) was spin-coated on an ITO transparent electrode and heat-treated (cured) at 220° C. for 30 minutes, thereby forming a hole injection layer having a thickness of 30 nm. A toluene solution including 2 wt % of α-NPD (N,N-di(1-naphthyl)-N,N-diphenyl-(1,1'-biphenyl)-4,4'-diamine) was spin-coated on the hole injection layer formed above, thereby forming a hole transport layer to have a thickness of 40 nm. Thereafter, that was transported into a vacuum deposition apparatus, and then 9,1-di-2-naphthalenyl-anthracene (ADN) and DPAVBi at a weight ratio (ADN:DPAVBi) of 20:1 were vacuum-deposited to have a thickness of 20 nm on the hole transport layer, thereby forming a light emitting layer. BCP was vacuum-deposited to have a thickness of 35 nm on the light emitting layer, thereby forming an electron injection and transport layer. LiF and aluminum were sequentially deposited on the electron injection and transport layer to have a thickness of 1 nm and 100 nm, respectively, thereby forming a cathode.

In the aforementioned procedure, the deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2\times10^{-7}$ torr to $5\times10^{-6}$ torr.

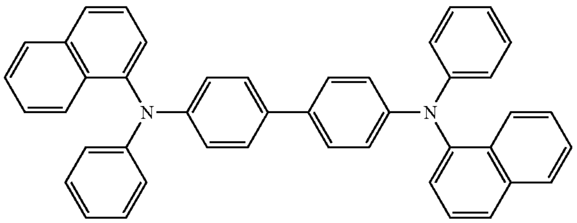

[α-NPD]

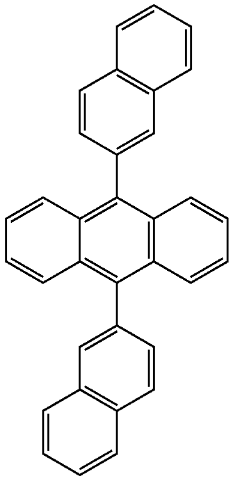

[ADN]

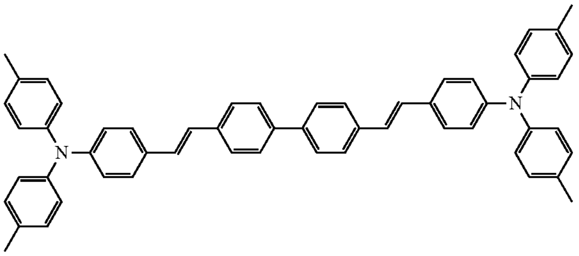

[DPAVBi(4,4'-Bis[4-(di-p-tolylamino)styryl]biphenyl)]

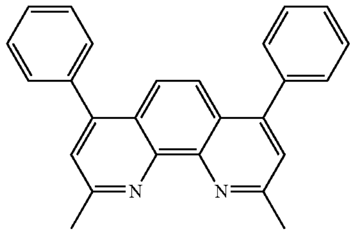

[BCP]

Example 2

An organic light emitting device was manufactured in the same manner as in Example 1, except that Compound 2 was used instead of Compound 1 in Example 1.

Example 3

An organic light emitting device was manufactured in the same manner as in Example 1, except that Compound 3 was used instead of Compound 1 in Example 1.

Comparative Example 1

An organic light emitting device was manufactured in the same manner as in Example 1, except that the following Comparative Compound 2 was used instead of Compound 1 in Example 1.

[Comparative Compound 2]

[Comparative Compound 2]

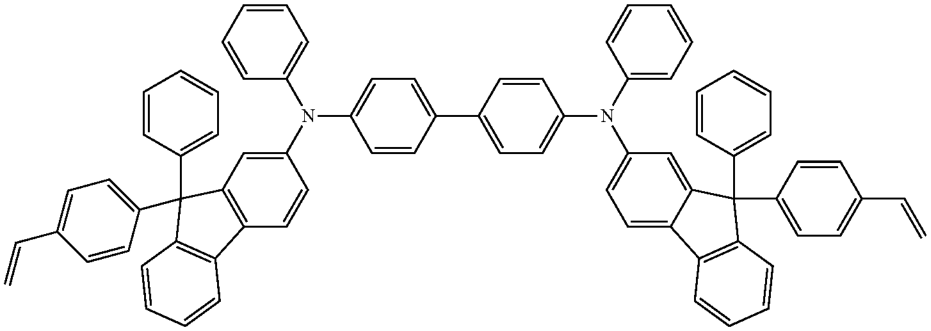 [SMILES: C=Cc1ccc(C2(c3ccccc3)c3ccccc3-c3ccc(N(c4ccccc4)c4ccc(-c5ccc(N(c6ccccc6)c6ccc7c(c6)C(c6ccccc6)(c6ccc(C=C)cc6)c6ccccc6-7)cc5)cc4)cc32)cc1]

Comparative Example 2

The present inventors tried to form a hole injection layer by using the following Comparative Compound 1 including no curable group instead of Compound 1 in Example 1 and form a hole transport layer by spin-coating a toluene solution including 2 wt % of NPD on the formed hole injection layer, but since Comparative Compound 1 was dissolved in a toluene solution including NPD, it was impossible to manufacture the device.

[Comparative Compound 1]

[Comparative Compound 1]

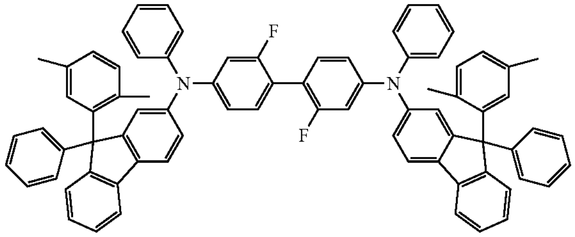

The results of measuring the performances of the organic light emitting devices manufactured in Examples 1 to 3 and Comparative Example 1 at a current density of 10 mA/cm$^2$ are shown in the following Table 2.

TABLE 2

| | Volt | J (mA/cm$^2$) | Cd/A | lm/A | QE (%) | Cd/m$^2$ | CIE$_x$ | CIE$_y$ | T95 (1000 cd/m$^2$) |
|---|---|---|---|---|---|---|---|---|---|
| Comparative Example 1 | 4.07 | 10.00 | 5.97 | 4.60 | 7.76 | 596.71 | 0.141 | 0.093 | 37.1 |
| Example 1 | 3.55 | 10.00 | 5.99 | 5.31 | 7.73 | 599.31 | 0.140 | 0.094 | 81.8 |
| Example 2 | 3.53 | 10.00 | 5.74 | 5.11 | 7.39 | 574.34 | 0.141 | 0.094 | 48.0 |
| Example 3 | 3.57 | 10.00 | 5.81 | 5.11 | 7.50 | 580.79 | 0.141 | 0.093 | 78.3 |

In Table 2, T95 means the time it takes for the luminescence to decrease to 95% from the initial luminescence.

As can be seen from Table 2, in the case of the compound into which F is introduced (Examples 1 to 3), it is possible to drive the device even at a low voltage, meaning that the compound has improved mobility compared to Comparative Compound 2 due to the introduction of F. Furthermore, it can be confirmed that the service lives of Examples 1 to 3 are improved compared to that of Comparative Example 1.

The invention claimed is:

1. A fluorene-based compound represented by the following Chemical Formula 1-1:

[Chemical Formula 1-1]

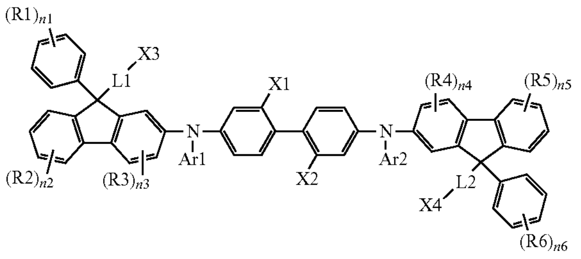

in Chemical Formula 1-1,

R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, L1 and L2 are the same as or different from each other, and are each independently a direct bond; or a substituted or unsubstituted alkylene group, Ar1 and Ar2 are the same as or different from each other, and are each independently a substituted or unsubstituted aryl group; or a substituted or unsubstituted heteroaryl group, X1 and X2 are the same as or different from each other, and are each independently hydrogen; or a halogen group, and at least one of X1 or X2 is a halogen group, X3 and X4 are the same as or different from each other, and are each independently deuterium; a substituted or unsubstituted alkyl group; a substituted or unsubstituted alkoxy group; a substituted or unsubstituted aryl group; a substituted or unsubstituted heteroaryl group; or a photocurable group or a thermosetting group, n1 and n6 are the same as or different from each other, and are each independently an integer from 0 to 5, n2 and n5 are the same as or different from each other, and are each independently an integer from 0 to 4, n3 and n4 are the same as or different from each other, and are each independently an integer from 0 to 3, and when n1 to n6 are each 2 or higher, each occurrence of R1 to R6 is the same as or different from each other.

2. The fluorene-based compound of claim 1, wherein the photocurable group or the thermosetting group is any one of the following structures:

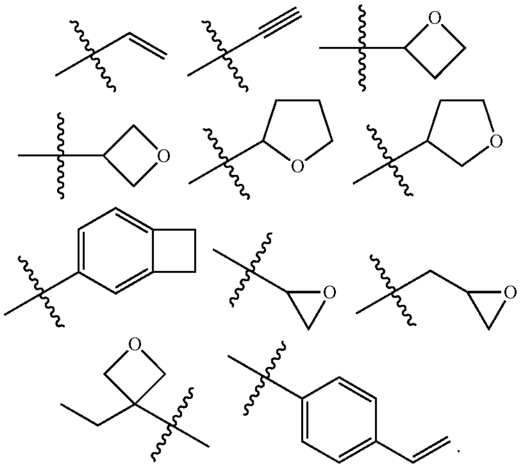

3. The fluorene-based compound of claim 1, wherein R1 to R6 are the same as or different from each other, and are each independently hydrogen; or a substituted or unsubstituted alkyl group having 1 to 30 carbon atoms.

4. The fluorene-based compound of claim 1, wherein Ar1 and Ar2 are the same as or different from each other, and are each independently a substituted or unsubstituted aryl group having 6 to 30 carbon atoms.

5. The fluorene-based compound of claim 1, wherein X3 and X4 are the same as or different from each other, and are each independently a photocurable group or a thermosetting group.

6. A fluorene-based compound represented by any one of the following structures:

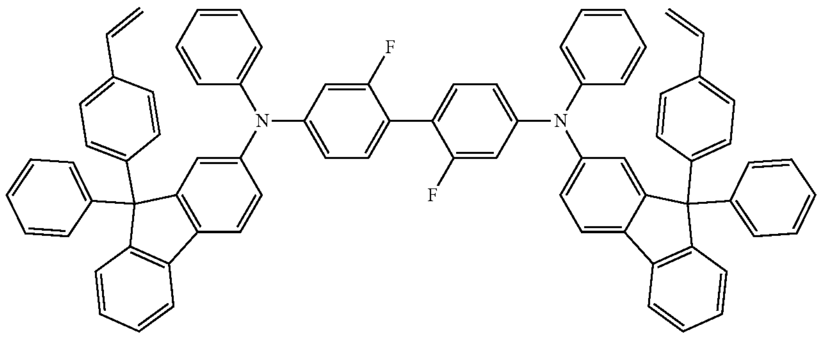

-continued
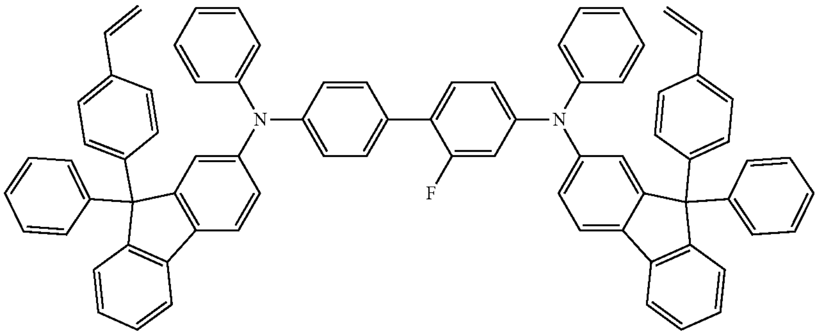
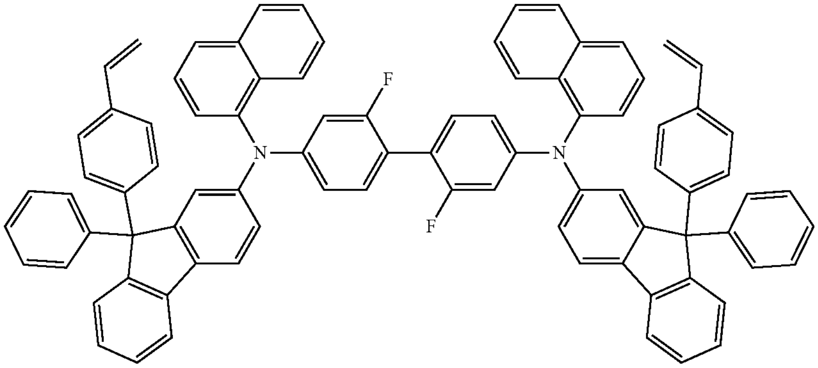
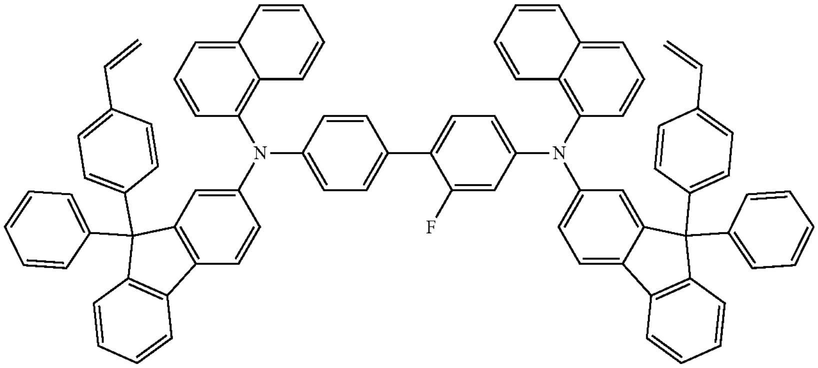
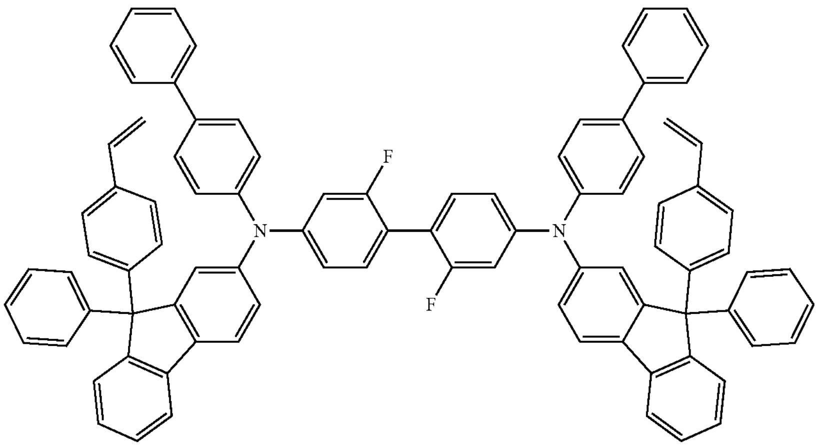

-continued
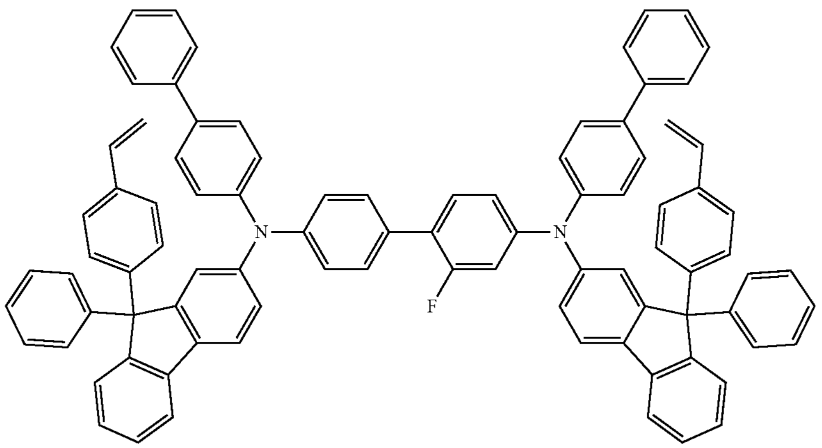
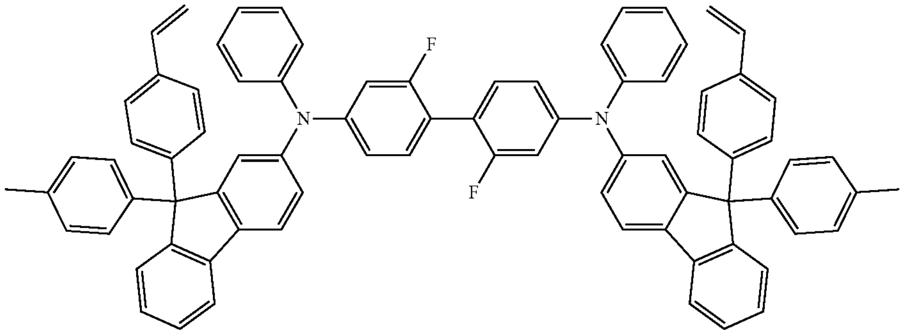
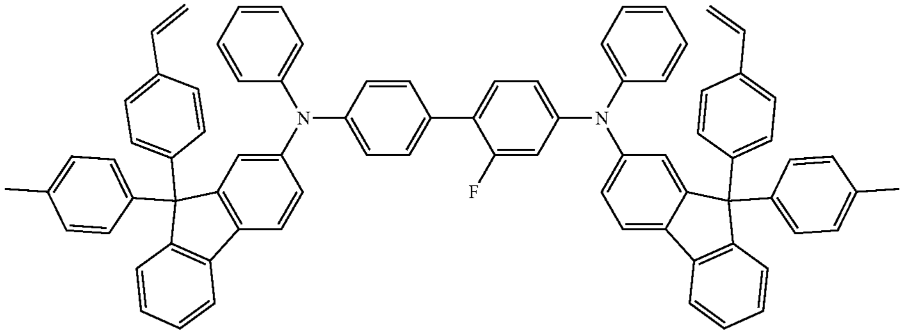
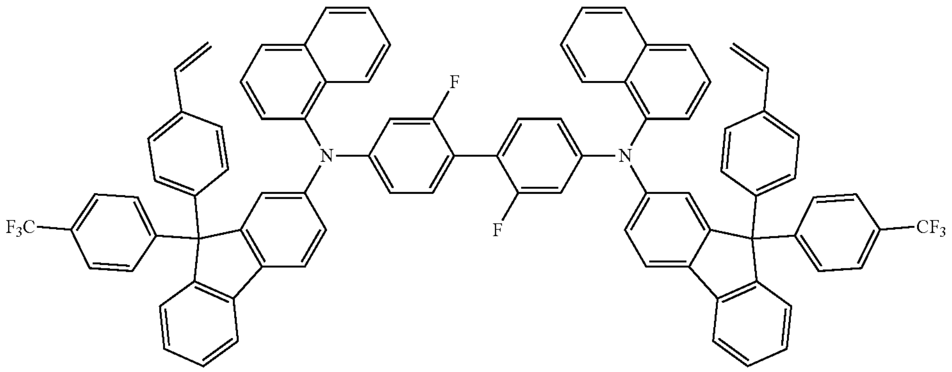

-continued
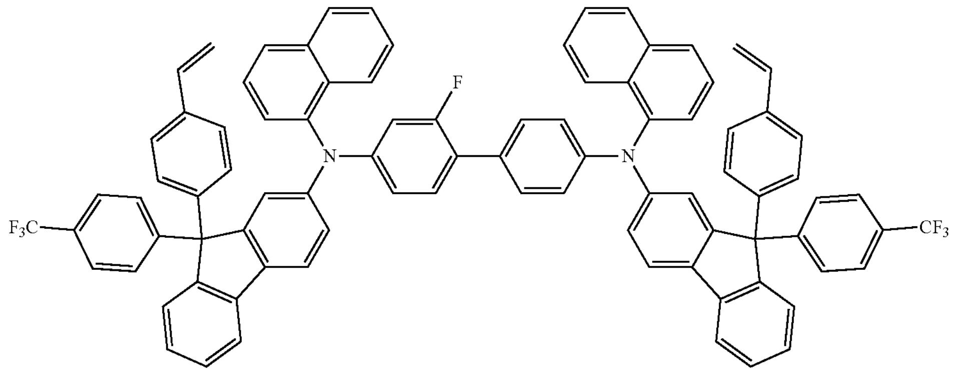
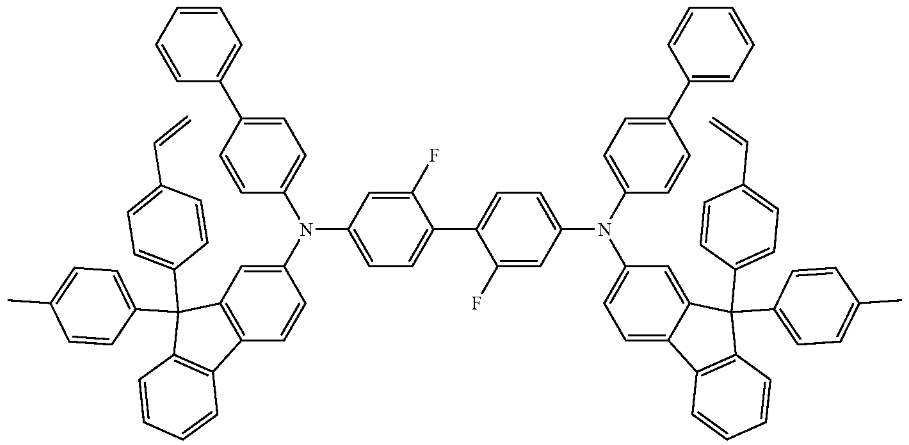
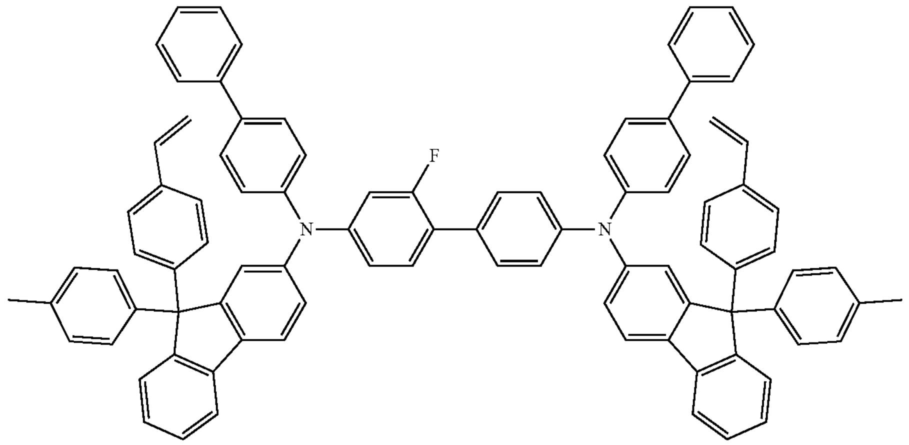
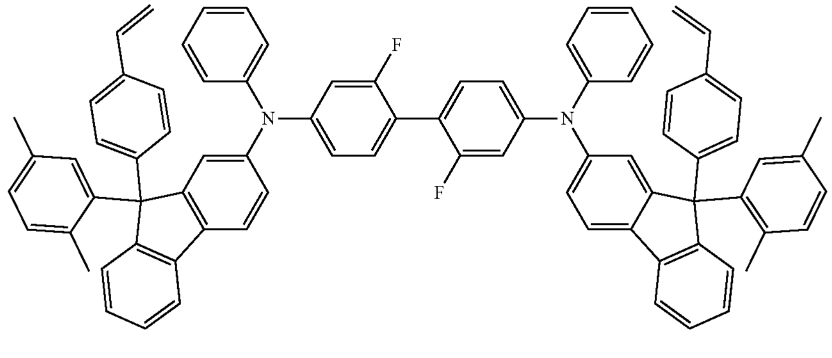

-continued
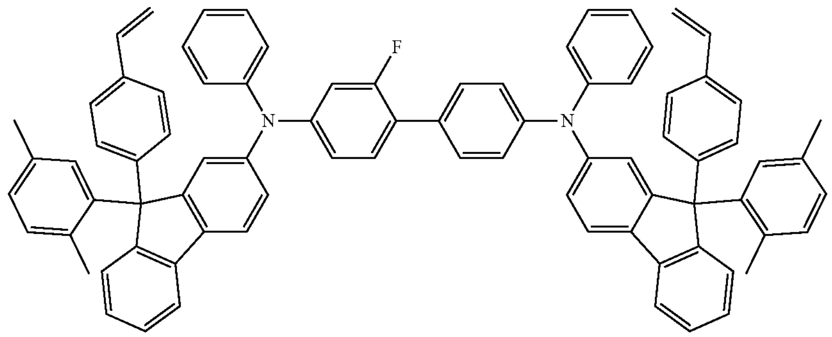
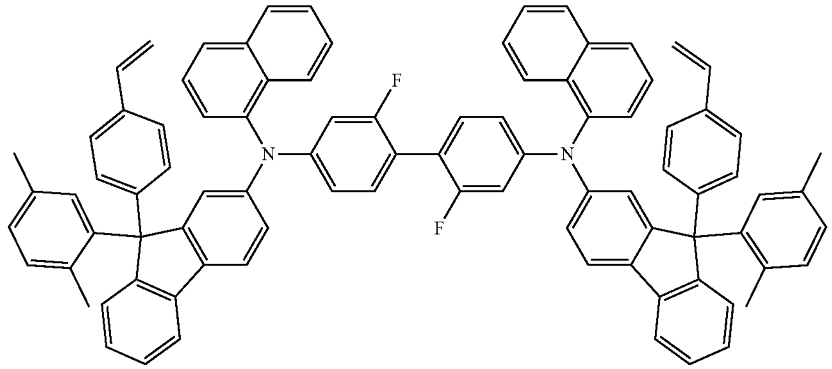
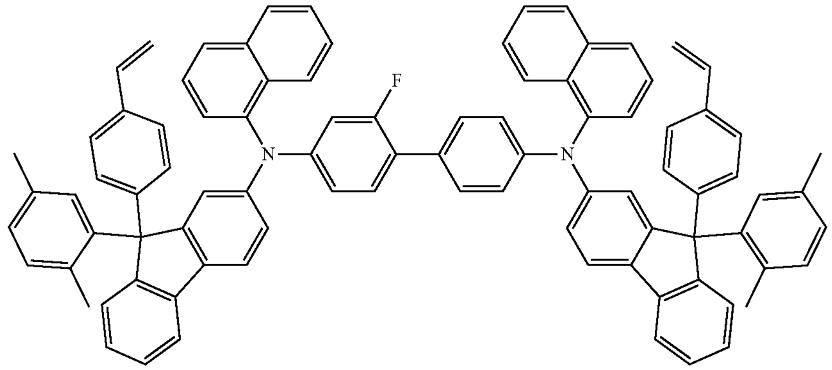
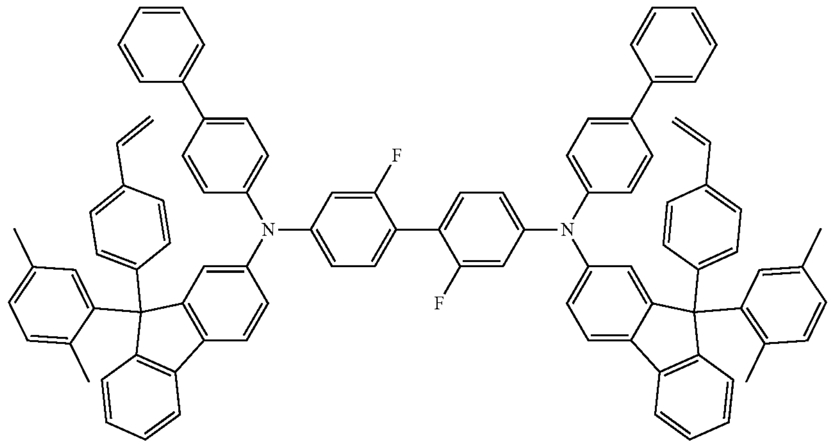

-continued
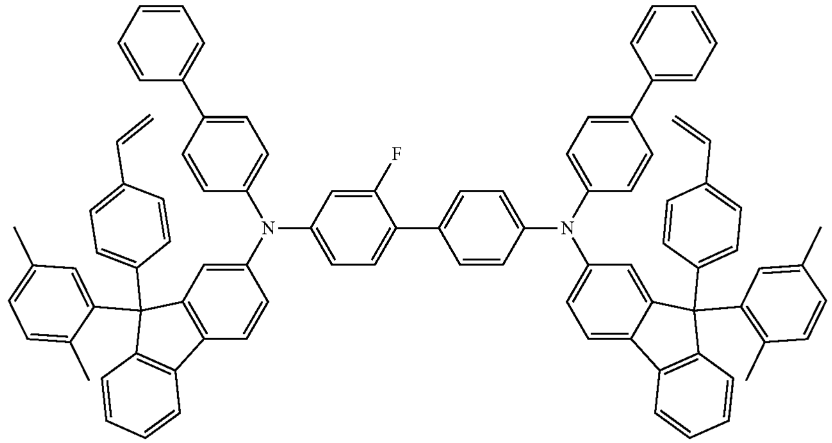
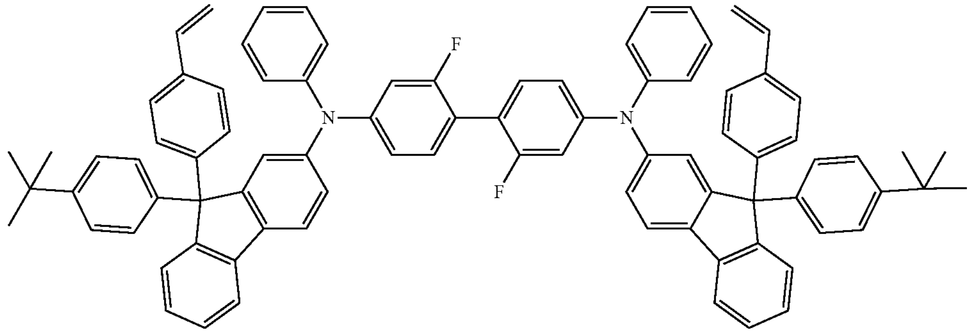
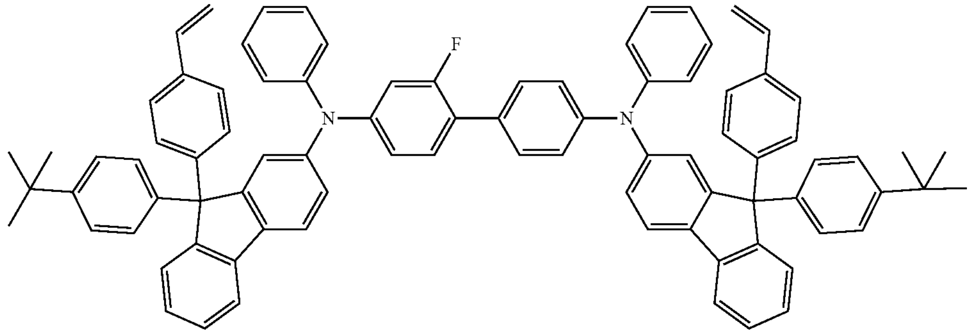
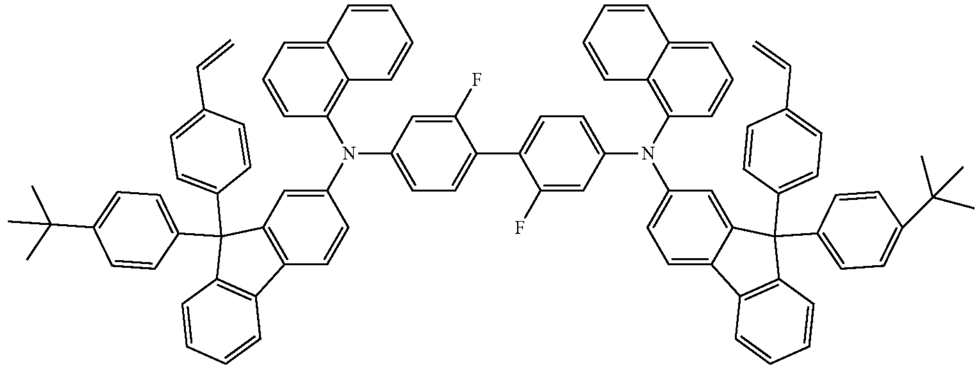

-continued

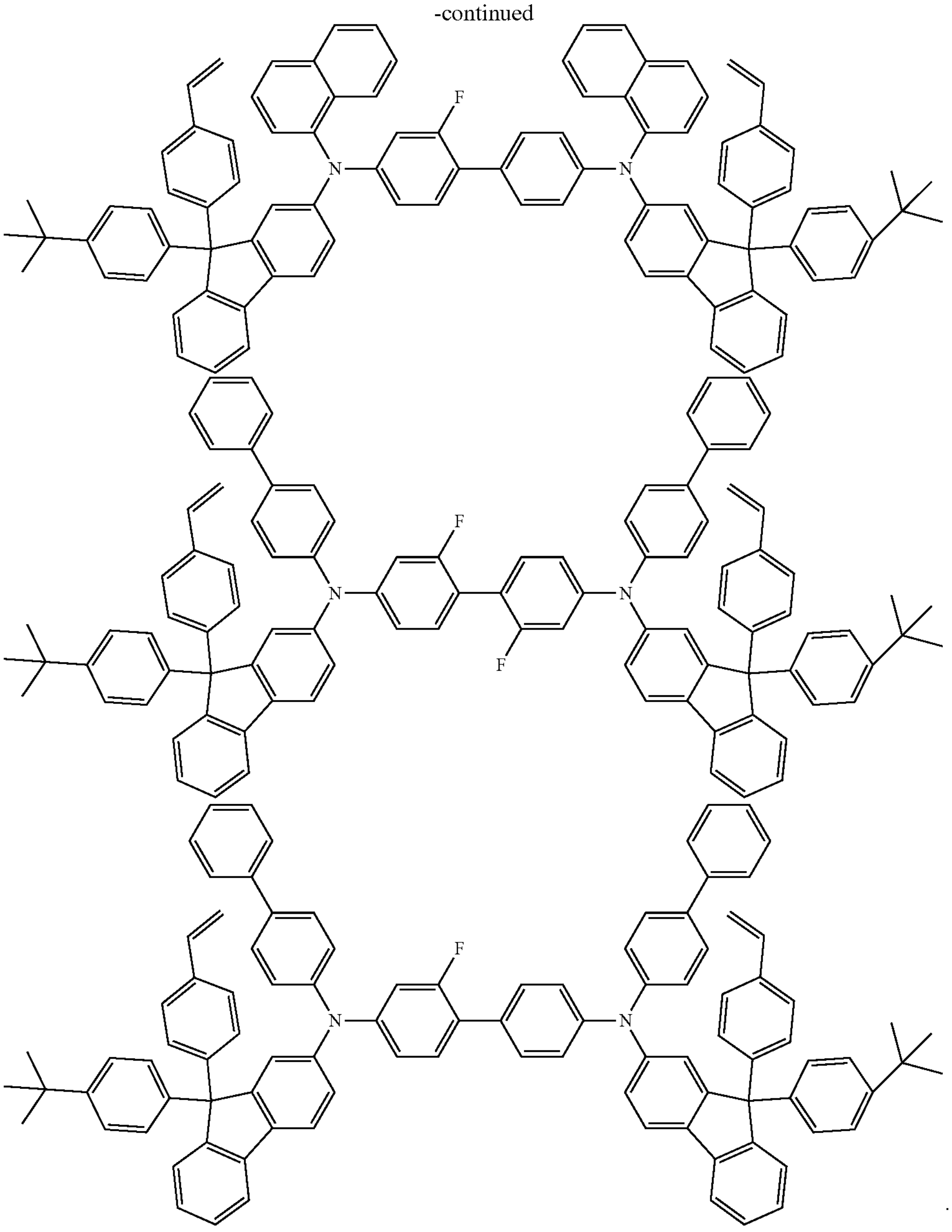

.

7. A coating composition comprising the fluorene-based compound of claim 1.

8. The coating composition of claim 7, further comprising a p-doping material.

9. The coating composition of claim 8, wherein the p-doping material is F4TCNQ; or a compound comprising a boron anion.

10. The coating composition of claim 7, further comprising: a single molecule compound comprising a thermosetting group or a photocurable group; or a single molecule compound comprising an end group capable of forming a polymer by heat.

11. An organic light emitting device comprising:

a first electrode;

a second electrode; and an organic material layer having one or more layers provided between the first electrode and the second electrode, wherein the one or more layers of the organic material layer comprise the coating composition of claim 7 or a cured product thereof, and the cured product of the coating composition is in a state in which the coating composition is cured by a heat treatment or a light treatment.

12. The organic light emitting device of claim 11, wherein the organic material layer comprising the coating composition or the cured product thereof is a hole transport layer, a hole injection layer, or a layer which simultaneously transports and injects holes.

13. A method of manufacturing an organic light emitting device, the method comprising:

preparing a substrate;

forming a first electrode on the substrate; forming an organic material layer having one or more layers on the first electrode; and forming a second electrode on the organic material layer, wherein the forming of the organic material layer comprises forming an organic material layer having one or more layers by using the coating composition of claim 7.

14. The method of claim 13, wherein the forming of the organic material layer by using the coating composition comprises:

coating the coating composition on the first electrode; and heat-treating or light-treating the coated coating composition.

15. The organic light emitting device of claim 11, wherein the organic material layer comprising the coating composition or the cured product thereof is a light emitting layer, and the light emitting layer includes the fluorene-based compound as a host.

* * * * *